United States Patent [19]

Takaya et al.

[11] Patent Number: 4,612,376
[45] Date of Patent: Sep. 16, 1986

[54] SUBSTITUTED-3,4-DIHYDRO-4-(2,4,6-TRIMETHOXYPHENYLIMINO)-2(1H)-PYRIMIDONES USEFUL AS CARDIOTONIC, ANTIHYPERTENSIVE, CEREBROVASCULAR VASODILATOR AND ANTI-PLATELET AGENT

[75] Inventors: Takao Takaya, Kawanishi; Masayoshi Murata, Osaka; Kiyotaka Ito, Ibaragi, all of Japan

[73] Assignee: Fujisawa Pharmaceutical Co., Ltd., Osaka, Japan

[21] Appl. No.: 588,902

[22] Filed: Mar. 12, 1984

[30] Foreign Application Priority Data

Mar. 25, 1983 [GB] United Kingdom ............... 8308290
Jun. 7, 1983 [GB] United Kingdom ............... 8315542
Oct. 18, 1983 [GB] United Kingdom ............... 8327859

[51] Int. Cl.⁴ ............... C07D 239/02; A61K 31/495
[52] U.S. Cl. ............... 544/317; 544/310; 544/311; 544/318
[58] Field of Search ............... 544/317, 310, 311, 318; 514/274

[56] References Cited

U.S. PATENT DOCUMENTS 3,923,807 12/1975 Fusukawa et al. ............... 260/256.4
4,400,506 8/1983 Lal et al. ............... 544/246

FOREIGN PATENT DOCUMENTS 10759 5/1980 European Pat. Off.
2008874 10/1970 Fed. Rep. of Germany.
2847693 5/1980 Fed. Rep. of Germany.
2032420 11/1970 France.
2073186 9/1971 France.
1296371 11/1972 United Kingdom.
1336138 11/1973 United Kingdom.

OTHER PUBLICATIONS

Taguchi et al., Chem. Abst., 88:5875r and J. Org. Chem. 1977, 42(125), 4127-31.
Maehr et al., Chem. Abst., 78:147903r, and J. Heterocyclic Chem., 1972, 9(6), 1389-94.
Ekpenyong et al., Chem. Abst., 89:197441m and Tetrahedron Lett., 1978 (19), 1619-22.
Lal et al., Chem. Abst., 93:220700m.
Taguchi et al., Chem. Abst., 91:211365g.
Yu et al., Chem. Abst., 89:23328q.
Chemical Abstracts, vol. 84, 1976, p. 478, No. 17404s, Columbus, OH & JP-A-75 53 381 (Ueda, Toru et al.), 12/05/1975.
Journal of the Chemical Society (Chem. Comm.), 1974, p. 959, London, GB; Shamshad Ahmed et al: "New Synthesis of Some 1,3-Oxazine Derivatives", p. 959.
Tetrahydron, vol. 37, No. 14, 1981, pp. 2451-2457, Oxford, GB., A. M. Lamazouere et al., "Tetrahydro-1,2,3,4 Pyrimidines et Octahydro-1,2,3,4,5,6,7,8 Quinazolines Dithiones-2,4 et Diones-2,4 Synthese et Etude du Mechanisme".
Johnson et al., J.A.C.S., vol. 37, (1915), pp. 378-383.

Primary Examiner—Donald G. Daus
Assistant Examiner—Cecilia Shen
Attorney, Agent, or Firm—Oblon, Fisher, Spivak, McClelland & Maier

[57] ABSTRACT

New pyrimidine derivatives of the formula:

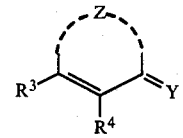

wherein
Z is a group selected from

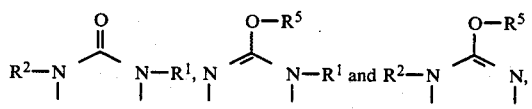

in which $R^1$ and $R^2$ are each hydrogen, alkenyl, ar(lower)alkyl or lower alkyl optionally substituted with epoxy, hydroxy, amino and/or lower alkylamino and $R^5$ is lower alkyl,
$R^3$ is hydrogen, aryl optionally substituted with lower alkyl, lower alkoxy and/or halogen, or pyridyl optionally substituted with lower alkyl,
$R^4$ is hydrogen, lower alkyl or phenyl optionally substituted with lower alkoxy, and
Y is =O, =S or =N—$R^6$, in which $R^6$ is lower alkyl; cyclo(lower)alkyl; ar(lower)alkyl optionally substituted with lower alkoxy; N-containing unsaturated heterocyclic group optionally substituted with lower alkyl; or aryl optionally substituted with hydroxy, lower alkyl, halogen or lower alkoxy, in which lower alkoxy substituent may be substituted with epoxy, hydroxy, amino and/or lower alkylamino,
provided that Y is =N—$R^6$ when $R^3$ and $R^4$ are each hydrogen, and Y is =S or =N—$R^6$ when $R^1$ and $R^2$ are each hydrogen or lower alkyl and $R^3$ is phenyl, and pharmaceutically acceptable salts thereof, and processes for preparation thereof and pharmaceutical composition comprising the same.

These derivatives and salts thereof are useful as cardiotonic, antihypertensive agent, cerebrovascular vasodilator and anti-platelet agent.

17 Claims, No Drawings

SUBSTITUTED-3,4-DIHYDRO-4-(2,4,6-TRIMETHOXYPHENYLIMINO)-2(1H)-PYRIMIDONES USEFUL AS CARDIOTONIC, ANTIHYPERTENSIVE, CEREBROVASCULAR VASODILATOR AND ANTI-PLATELET AGENT

This invention relates to new pyrimidine derivatives. More particularly, this invention relates to new pyrimidine derivatives and pharmaceutically acceptable salts thereof which have pharmacological activities, processes for preparation thereof, a pharmaceutical composition comprising the same and method of use thereof.

Accordingly, one object of this invention is to provide the new and useful pyrimidine derivatives and pharmaceutically acceptable salt thereof.

Another object of this invention is to provide processes for preparation of the pyrimidine derivatives and pharmaceutically acceptable salts thereof.

A further object of this invention is to provide a pharmaceutical composition comprising said pyrimidine derivative or pharmaceutically acceptable salt thereof as a cardiotonic, antihypertensive agent, cerebrovascular vasodilator and anti-platelet agent.

Still further object of this invention is to provide a method of using said pyrimidine derivative or a pharmaceutically acceptable salt thereof for therapeutic treatment of heart disease, hypertension, cerebrovascular disease and thrombosis of human being and animals.

Some pyrimidine derivatives having antihypertensive and vasodilative activities have been known as described, for example, in European Patent Publication No. 0010759.

The pyrimidine derivatives of this invention are novel and represented by the following general formula [I]:

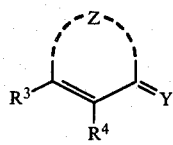

wherein
Z is a group selected from

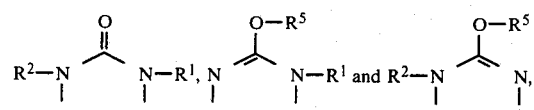

in which $R^1$ and $R^2$ are each hydrogen, alkenyl, ar(lower)alkyl or lower alkyl optionally substituted with epoxy, hydroxy, amino and/or lower alkylamino and $R^5$ is lower alkyl, $R^3$ is hydrogen, aryl optionally substituted with lower alkyl, lower alkoxy and/or halogen, or pyridyl optionally substituted with lower alkyl, $R^4$ is hydrogen, lower alkyl or phenyl optionally substituted with lower alkoxy, and Y is =O, =S or =N—$R^6$, in which $R^6$ is lower alkyl; cyclo(lower)alkyl; ar(lower)alkyl optionally substituted with lower alkoxy; N-containing unsaturated heterocyclic group optionally substituted with lower alkyl; or aryl optionally substituted with hydroxy, lower alkyl, halogen and/or lower alkoxy, in which lower alkoxy substituent may be substituted with epoxy, hydroxy, amino and/or lower alkylamino, provided that Y is =N—$R^6$ when $R^3$ and $R^4$ are each hydrogen, and Y is =S or =N—$R^6$ when $R^1$ and $R^2$ are each hydrogen or lower alkyl and $R^3$ is phenyl.

As to the object compound [I], the following points are to be noted. That is, when Z is a group of the formula:

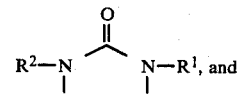

$R^1$ and/or $R^2$ are hydrogen, then the pyrimidine moiety in the object compound [I] can be alternatively represented by its tautomers. For example, when both of $R^1$ and $R^2$ are hydrogen and Y is =N—$R^6$, the compound [I] can be represented by one of the structural formula (A) to (E) as shown in the following.

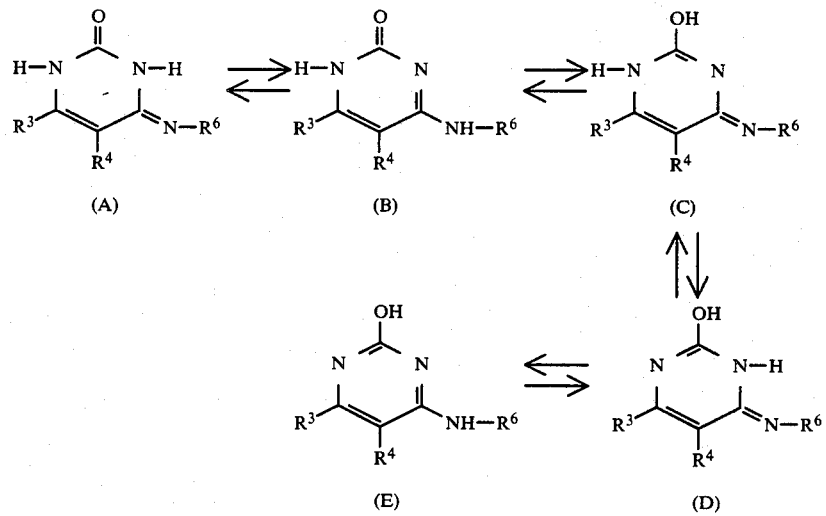

wherein $R^3$, $R^4$ and $R^6$ are each as defined above.

The object compound may be presented in any of these tautomeric forms and may co-exist in an equilibrium mixture. Accordingly all of these tautomeric forms are included within the scope of the present invention.

In case that Y is =O or =S, the pyrimidine moiety in the object compound [I] also includes its tautomeric isomers, and can be represented by substantially the same tautomerism as illustrated above.

In the present specification, however, the object compound [I] is represented by the above formula (A) only for the convenient sake.

The object compound [I] and their salts of the present invention can be prepared by the following processes.

Process 1

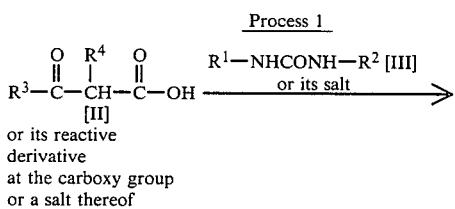

[II]
or its reactive
derivative
at the carboxy group
or a salt thereof

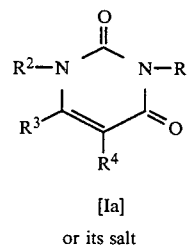

[Ia]
or its salt

Process 2

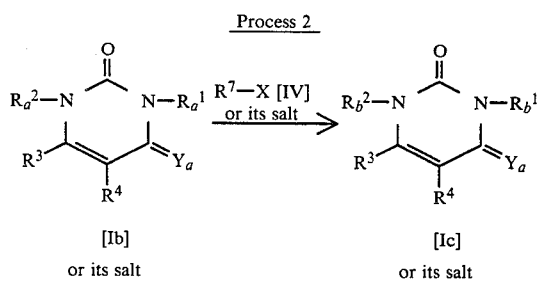

[Ib]     [Ic]
or its salt     or its salt

Process 3

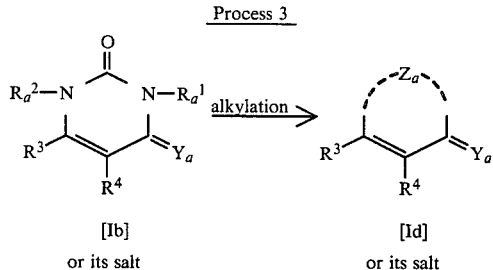

[Ib]     [Id]
or its salt     or its salt

Process 4

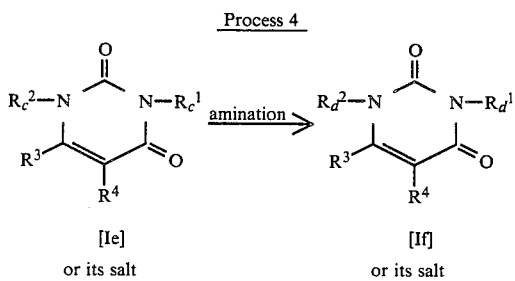

[Ie]     [If]
or its salt     or its salt

Process 5

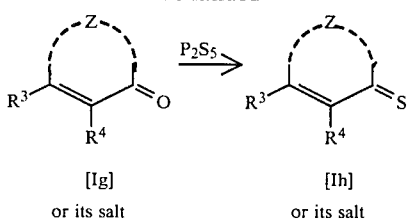

[Ig]     [Ih]
or its salt     or its salt

Process 6

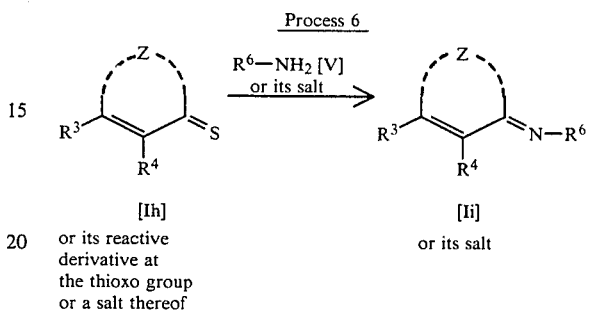

[Ih]     [Ii]
or its reactive     or its salt
derivative at
the thioxo group
or a salt thereof

Process 7

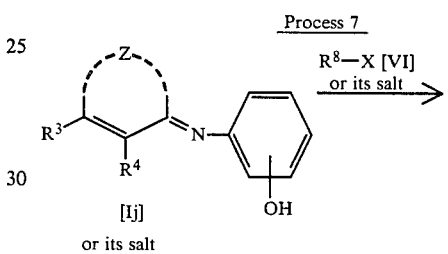

[Ij]
or its salt

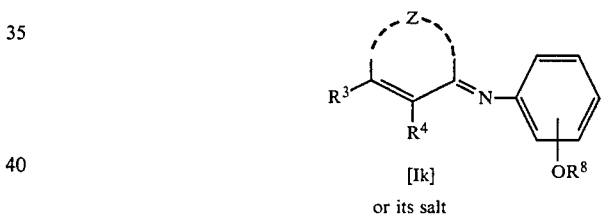

[Ik]
or its salt

Process 8

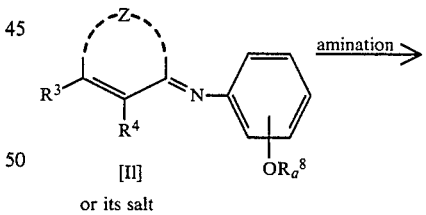

[Il]
or its salt

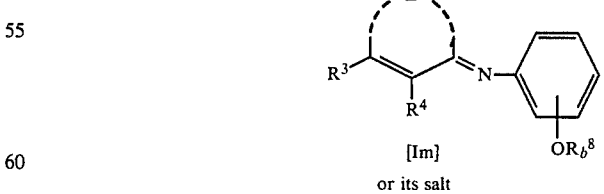

[Im]
or its salt wherein
$R^1$, $R^2$, $R^3$, $R^4$, $R^6$ and Z are each as defined above,
one of $R_a^1$ and $R_a^2$ is hydrogen and another is hydrogen, alkenyl, ar(lower)alkyl or lower alkyl optionally substituted with epoxy, hydroxy, amino and/or lower alkylamino, one of $R_b^1$ and $R_b^2$ is alkenyl, ar(lower)alkyl or lower alkyl optionally substituted with epoxy, hydroxy, amino and/or lower alkylamino and another is hydrogen, alkenyl, ar(lower)alkyl or lower alkyl optionally substituted with epoxy, hydroxy, amino and/or lower alkylamino, one of $R_c^1$ and $R_c^2$ is lower alkyl which is substituted with epoxy and another is hydrogen, alkenyl, ar(lower)alkyl or lower alkyl optionally substituted with epoxy, hydroxy, amino and/or lower alkylamino, one of $R_d^1$ and $R_d^2$ is lower alkyl which is substituted with hydroxy and amino or lower alkylamino and another is hydrogen, alkenyl, ar(lower)alkyl or lower alkyl optionally substituted with hydroxy, amino and/or lower alkylamino, $R^7$ is alkenyl, ar(lower)alkyl or lower alkyl optionally substituted with epoxy, hydroxy, amino and/or lower alkylamino, $R^8$ is lower alkyl optionally substituted with epoxy, hydroxy, amino and/or lower alkylamino, $R_a^8$ is lower alkyl substituted with epoxy, $R_b^8$ is lower alkyl substituted with hydroxy and amino or lower alkylamino, X is a leaving group, $Y_a$ is =O or =N—$R^6$, in which $R^6$ is as defined above, and $Z_a$ is a group of the formula:

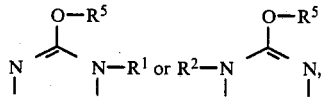

in which $R^1$, $R^2$ and $R^5$ are each as defined above, provided that Y is =N—$R^6$ when $R^3$ and $R^4$ are each hydrogen, and Y is =S or =N—$R^6$ when $R^1$ and $R^2$ are each hydrogen or lower alkyl and $R^3$ is phenyl.

In the above and subsequent description of the present specification, suitable examples and illustrations for the various definitions to be included within the scope of the invention are explained in detail as follows.

It is to be noted, however, that the definitions of $R_a^1$, $R_b^1$, $R_c^1$ and $R_d^1$ are included in the scope of the definition of $R^1$, and that the definitions of $R_a^2$, $R_b^2$, $R_c^2$ and $R_d^2$ are included in the scope of the definition of $R^2$, and that the definitions of $R_a^8$ and $R_b^8$ are also included in the scope of the definition of $R^8$. Accordingly, the suitable examples and illustrations for $R_a^1$ to $R_d^1$, $R_a^2$ to $R_d^2$ and $R_a^8$ to $R_b^8$ are to be referred to those for $R^1$, $R^2$ and $R^8$, respectively.

The term "lower" is intended to mean 1 to 6 carbon atom(s) unless otherwise indicated.

Suitable examples of lower alkyl for $R^1$, $R^2$, $R^4$, $R^5$, $R^6$, $R^7$ and $R^8$ may be a straight or branched one such as methyl, ethyl, propyl, isopropyl, butyl, isobutyl, tert-butyl, pentyl, hexyl or the like.

The lower alkyl group for $R^1$, $R^2$, $R^7$ and $R^8$ may be substituted with epoxy, hydroxy, amino, and/or lower alkylamino [e.g. methylamino, ethylamino, propylamino, butylamino, t-butylamino, pentylamino, hexylamino, etc.].

Suitable examples of the lower alkyl group having such substitutent(s) may be epoxy substituted lower alkyl [e.g. 2,3-epoxypropyl, 3,4-epoxybutyl, 4,5-epoxypentyl, 4,6-epoxyhexyl, etc.], hydroxy substituted lower alkyl [e.g. hydroxymethyl, 2-hydroxyethyl, 2-hydroxypropyl, 3-hydroxypropyl, 6-hydroxyhexyl, etc.], amino substituted lower alkyl [e.g. aminomethyl, 1-aminoethyl, 2-aminoethyl, 2-aminopropyl, 3-aminopropyl, 4-aminobutyl, 5-aminopentyl, 6-aminohexyl, etc.], lower alkylamino substituted lower alkyl [e.g. methylaminomethyl, dimethylaminomethyl, 2-(methylamino)ethyl, 2-(diethylamino)ethyl, 2-(methylamino)propyl, 3-(ethylamino)propyl, 3-(isopropylamino)propyl, 3-(t-butylamino)propyl, 6-(hexylamino)hexyl, etc.], hydroxy and lower alkylamino substituted lower alkyl [e.g. 2-hydroxy-3-methylaminopropyl, 3-hydroxy-2-methylaminopropyl, 2-hydroxy-3-isopropylaminopropyl, 3-butylamino-2-hydroxypropyl, 2-t-butylamino-3-hydroxypropyl, 3-t-butylamino-2-hydroxypropyl, etc.], or the like.

Suitable examples of alkenyl for $R^1$, $R^2$ and $R^7$ may be vinyl, allyl, propenyl, isopropenyl, butenyl, pentenyl or the like.

Suitable examples of ar(lower)alkyl for $R^1$, $R^2$ and $R^7$ may be benzyl, phenethyl, 3-phenylpropyl, benzhydryl, trityl or the like.

Suitable examples of aryl for $R^3$ and $R^6$ may include phenyl, naphthyl and the like.

The aryl group for $R^3$ may be optionally substituted with lower alkoxy [e.g. methoxy, ethoxy, propoxy, isopropoxy, butoxy, isobutoxy, tert-butoxy, pentyloxy, hexyloxy, etc.], halogen [e.g. chlorine, bromine, fluorine, iodine] and/or the aforementioned lower alkyl.

Suitable examples of the aryl group for $R^3$ having such substituent(s) may be lower alkoxy substituted phenyl [e.g. 4-methoxyphenyl, 3,4-dimethoxyphenyl, 3,4,5-trimethoxyphenyl, 2,3,4-trimethoxyphenyl, 2-ethoxyphenyl, 4-hexyloxyphenyl, etc.], halogenated phenyl [e.g. 2-chlorophenyl, 4-chlorophenyl, 2,4-dichlorophenyl, 3,4-dichlorophenyl, 2,6-dichlorophenyl, 2-bromophenyl, 2-bromo-4-chlorophenyl, etc.], lower alkoxy and halogen substituted phenyl [e.g. 3-chloro-4-methoxyphenyl, 4-chloro-2-methoxyphenyl, 3-chloro-4,5-dimethoxyphenyl, 2-bromo-4-ethoxyphenyl, etc.], lower alkyl substituted phenyl [e.g. p-tolyl, o-tolyl, 4-ethylphenyl, 4-hexylphenyl, 2,6-dimethylphenyl, 3,4-dimethylphenyl, 2,4,6-trimethylphenyl, etc.], lower alkyl and halogen substituted phenyl [e.g. 4-chloro-2-methylphenyl, 4-chloro-2-ethylphenyl, 2-bromo-3-methylphenyl, etc.], or lower alkoxy and lower alkyl substituted phenyl [e.g. 2-methyl-4-methoxyphenyl, 2-ethyl-4-methoxyphenyl, 3-ethyl-4-ethoxyphenyl, etc.].

The pyridyl group for $R^3$ may include pyridyl [e.g. 2-pyridyl, 3-pyridyl and 4-pyridyl] and pyridinio, and these pyridyl groups may be optionally substituted with the aforementioned lower alkyl.

Suitable examples of the pyridyl group for $R^3$ having such substituent(s) may be 2-methylpyridyl, 3-ethylpyridyl, 3-ethyl-6-methylpyridyl, 1-methylpyridinio, 1-ethylpyridinio, 1-hexylpyridinio or the like.

The phenyl group for $R^4$ may be optionally substituted with lower alkoxy group, suitable examples of which can be referred to those as exemplified for the lower alkoxy substituted phenyl for $R^3$.

Suitable examples of cyclo(lower)alkyl for $R^6$ may be cyclopropyl, cyclobutyl, cyclopentyl, cyclohexyl or the like.

The aryl group for $R^6$ may be optionally substituted with hydroxy, lower alkyl, halogen and/or lower alkoxy, in which lower alkoxy substituent may be substituted with epoxy, hydroxy, amino and/or lower alkylamino.

Suitable examples of the aryl group for $R^6$ having such substituent(s) may be lower alkyl substituted phenyl, halogenated phenyl, lower alkyl and halogen substituted phenyl, lower alkoxy substituted phenyl as exemplified before for $R^3$, respectively, or hydroxy substituted phenyl [e.g. 2-hydroxyphenyl, 3-hydroxyphenyl, 4-hydroxyphenyl, etc.]. The lower alkoxy moiety of said lower alkoxy substituted phenyl group may be further substituted with epoxy, hydroxy, amino and/or lower alkylamino. Suitable examples of the lower alkoxy substituted phenyl having these additional substituent(s) may be 4-(2,3-epoxypropoxy)phenyl, 2-(hydroxymethoxy)phenyl, 4-(2-aminoethoxy)phenyl, 4-(3-methylaminopropoxy)phenyl, 4-(2-hydroxy-3-isopropylaminopropoxy)phenyl, 4-(3-t-butylamino-2-hydroxypropoxy)phenyl or the like.

Suitable examples of ar(lower)alkyl for $R^6$ may be benzyl, phenethyl, 3-phenylpropyl, benzhydryl, trityl or the like. Said ar(lower)alkyl groups may be optionally substituted with the aforementioned lower alkoxy, and suitable examples of the ar(lower)alkyl group having such substituent(s) may be lower alkoxy substituted benzyl [e.g. 4-methoxybenzyl, 2-ethoxybenzyl, 3,4-dimethoxybenzyl, etc.], lower alkoxy substituted benzhydryl [e.g. 4-methoxybenzhydryl, 4,4'-dimethoxybenzhydryl, etc.] or the like.

Suitable examples of N-containing unsaturated heterocyclic group for $R^6$ may be 5- or 6-membered N-containing unsaturated heterocyclic group such as pyrrolyl, imidazolyl, imidazolinyl, pyrazolyl, pyridyl, pyrazinyl, pyrimidinyl, pyridazinyl, thiazolyl, isothiazolyl, thiadiazolyl, [e.g. 1,2,3-thiadiazolyl, 1,2,4-thiadiazolyl, 1,3,4-thiadiazolyl, etc.] or the like. These N-containing unsaturated heterocyclic groups may be substituted with lower alkyl as exemplified before. Suitable examples of the N-containing unsaturated heterocyclic group having such substituent(s) may be 4-methylpyridyl, 2,4,6-trimethylpyridyl, 5-methyl-1,3,4-thiadiazolyl or the like.

Suitable examples of the leaving group for X may be halide [e.g. chloride, bromide, iodide, etc.], sulfonate [e.g. methanesulfonate, benzenesulfonate, toluenesulfonate, etc.] or the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], and the like.

In this respect, it is to be noted that the compounds [Ia] to [Im] are included within the scope of the compound [I], and accordingly the suitable salts of these compounds [Ia] to [Im] are to be referred to those as exemplified for the object compound [I] in the above.

The processes for preparing the object compound [I] and salts thereof are explained in detail in the following.

PROCESS 1

The object compound [Ia] and its salt can be prepared by reacting a compound [II] or its reactive derivative at the carboxy group or a salt thereof with a compound [III] or its salt.

Suitable salts of the compounds [II] and [III] may be the same as those exemplified for the compound [I].

Suitable reactive derivative at the carboxy group of the compound [II] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like. These reactive derivatives can be optionally selected according to the kind of the compound [II] to be used.

This reaction is usually carried out in a conventional solvent such as water, methanol, ethanol, propanol, tetralin, tetrahydrofuran, dioxane, chloroform, toluene, dimethylformamide, dimethylsulfoxide or any other organic solvent which does not adversely influence the reaction.

This reaction is preferably conducted in the presence of an acid such as inorganic acid [e.g. hydrochloric acid, sulfuric acid, polyphosphoric acid, etc.], organic acid [e.g. trifluoroacetic acid, benzenesulfonic acid, toluenesulfonic acid, etc.] or the like.

The reaction can also be conducted under dehydrating condition such as an azeotropic dehydration, in the presence of a dehydrating agent [e.g. magnesium sulfate, anhydrous zinc chloride, phosphorus pentoxide, zeolite, silica gel, etc.] or the like.

In case that the compound [II] is used in a free acid form or its salt form, the reaction is preferably carried out in the presence of a conventional condensing agent.

The reaction temperature is not critical, and the reaction is usually carried out at ambient temperature or under warming or heating.

PROCESS 2

The object compound [Ic] and its salt can be prepared by reacting a compound [Ib] or its salt with a compound [IV] or its salt.

Suitable salts of the compound [IV] may be the same as those exemplified for the compound [I].

This reaction is preferably conducted in the presence of a base such as alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal alkoxide [e.g. sodium methoxide, sodium ethoxide, potassium tert-butoxide, etc.] or the like.

This reaction is usually carried out in a conventional solvent such as water, methanol, ethanol, propanol, tetrahydrofuran, dioxane, acetonitrile, methylene chloride, chloroform, benzene, dimethylformamide, dimethyl sulfoxide or any other organic solvent which does not adversely influence the reaction. These solvent can be optionally selected according to the kinds of the starting compound [Ib], the base and the compound [IV], especially to the kind of the base to be used.

The reaction temperature is not critical, and the reaction is usually carried out at ambient temperature or under warming or heating.

PROCESS 3

The object compound [Id] and its salt can be prepared by alkylating a compound [Ib] or its salt.

This reaction is carried out in substantially the same manner as that of Process 2, and therefore the reaction mode and reaction conditions [e.g. base, solvent, reaction temperature, etc.] of this process are to be referred to those as explained in Process 2.

PROCESS 4

The object compound [If] and its salt can be prepared by reacting a compound [Ie] or its salt with ammonia or lower alkyl amine or a salt thereof.

Suitable salts of ammonia and the lower alkyl amine may be acid addition salts as exemplified for the compound [I].

Suitable examples of the lower alkyl amine to be used in this reaction may include primary and secondary amine such as methylamine, ethylamine, propylamine, butylamine, t-butylamine, pentylamine, hexylamine, dimethylamine, diethylamine, dipropylamine, diisopropylamine, dibutylamine, dihexylamine and the like.

This reaction is usually carried out in a conventional solvent such as water, methanol, ethanol, tetrahydrofuran, dioxane, methylene chloride, chloroform, benzene, dimethylformamide, dimethyl sulfoxide or any other organic solvent which does not adversely influence the reaction.

The reaction temperature is not critical, and the reaction is usually carried out at ambient temperature or under warming or heating.

PROCESS 5

The object compound [Ih] and its salt can be prepared by reacting a compound [Ig] or its salt with phosphorus pentasulfide.

This reaction is usually carried out in a conventional solvent such as benzene, toluene, xylene, pyridine, tetrahydrofuran, dioxane or any other organic solvent which does not adversely influence the reaction.

The reaction temperature is not critical, and the reaction is usually carried out under warming or heating.

PROCESS 6

The object compound [Ii] and its salt can be prepared by reacting a compound [Ih] or its reactive derivative at the thioxo group or a salt thereof with a compound [V] or its salt.

Suitable salts of the compound [V] may be the same as those exemplified for the compound [I].

This reaction is usually carried out in a conventional solvent such as methanol, ethanol, propanol, tetrahydrofuran, dioxane, methylene chloride, dimethylformamide or any other organic solvent which does not adversely influence the reaction. In case that the compound [V] is liquid, it can also be used as a solvent.

The reaction temperature is not critical, and the reaction is usually carried out at ambient temperature or under warming or heating.

In case that the group $-O-R^5$ is included in the group Z of the starting compound [Ih], the lower alkyl moiety for $R^5$ is occasionally removed in this process to give a ketone compound.

Suitable reactive derivative at the thioxo group of the compound [Ih] may be S-alkyl derivative [e.g. S-methyl derivative, S-ethyl derivative, S-octyl derivative, etc.], S-ar(lower)alkyl derivative [e.g. S-benzyl derivative, etc.] or the like. These reactive derivatives can be prepared by reacting a compound [Ih] or its salt with an alkylating agent such as alkyl halide [e.g. methyl iodide, ethyl iodide, octyl bromide, etc.], ar(lower)alkyl halide [e.g. benzyl chloride, benzyl bromide, etc.] or the like. This reaction is carried out in substantially the same manner as that of Process 2, and therefore the reaction mode and reaction conditions [e.g. solvent, reaction temperature, etc.] of the reaction are to be referred to those as explained in Process 2.

PROCESS 7

The object compound [Ik] and its salt can be prepared by reacting a compound [Ij] or its salt with a compound [VI] or its salt.

Suitable salts of the compound [VI] may be acid addition salts as exemplified for the compound [I].

This reaction is carried out in substantially the same manner as that of Process 2, and therefore the reaction mode and reaction conditions [e.g. base, solvent, reaction temperature, etc.] of this process are to be referred to those as explained in Process 2.

PROCESS 8

The object compound [Im] and its salt can be prepared by aminating a compound [Il] or its salt.

This reaction is carried out in substantially the same manner as that of Process 4, and therefore the reaction mode and reaction conditions [e.g. aminating agent, solvent, reaction temperature, etc.] of this process are to be referred to those as explained in Process 4.

Among the starting compound [II], new compounds may be obtained by any process known in the art for preparing structurally analogous compound thereto.

It is to be noted that each of the object compound [I] and the starting compounds [II], [III], [IV], [V] and [VI] include one or more stereoisomers due to asymmetric carbon atoms in the molecule, and all of such isomers of the compounds [I], [II], [III], [IV], [V] and [VI] are included within the scope of this invention.

The new pyrimidine derivatives [I] and pharmaceutical acceptable salts thereof possess a cardiotonic activity, anti-platelet activity, cerebrovascular vasodilative activity and antihypertensive activity, and are useful for a therapeutic treatment of heart disease [e.g. cardiac insufficiency, etc.], thombosis, cerebrovascular disease and hypertension.

For the purpose of showing pharmaceutical activity of the pyrimidine derivatives [I], cardiotonic test data, inhibitory activity test data on platelet aggregation, cerebrovascular vasodilative test data and antihypertensive test data are illustrated in the following.

Test Method A (Cardiotonic activity):

Mongrel dogs of either sex were anesthetized with sodium pentobarbital, 35 mg/kg, i.p.. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure, from which dp/dt max was derived by analog computing. To measure the systemic blood pressure the left femoral artery was cannulated. The blood pressure pulse was used to trigger a heart rate meter. Another catheter was positioned in the vena cave through right femoral vein for injection of drugs. Systemic blood pressure, left ventricular pressure, dp/dt max and heart rate were recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max changes (dp/dt M.C) calculated by following formula, and are shown in table 1.

$$dp/dt\ M.C\ (\%) = \left( \frac{dp/dt\ \text{max after dosing}}{dp/dt\ \text{max before dosing}} - 1 \right) \times 100$$

Test Results A

TABLE 1

| Test Compound (Example No.) | Dose (mg/kg) | dp/dt M. C. (%) |
|---|---|---|
| Example 48 | 0.01 | 43.0 |
| Example 49 | 0.1 | 68.0 |
| Example 50 | 1.0 | 98.0 |
| Example 56 | 0.1 | 44.0 |
|  | 1.0 | 88.0 |
| Example 57 | 0.1 | 60.0 |
|  | 1.0 | 126.0 |
| Example 58 | 0.1 | 84.0 |
|  | 1.0 | 145.0 |
| Example 59 | 0.1 | 57.0 |
|  | 1.0 | 158.0 |
| Example 62 | 1.0 | 102.0 |
| Example 64 | 0.1 | 98.0 |
|  | 1.0 | 93.0 |
| Example 65 | 0.1 | 50.0 |
|  | 1.0 | 206.0 |
| Example 69 | 0.01 | 45.0 |
|  | 0.1 | 42.0 |
| Example 72 | 0.01 | 12.0 |
|  | 0.1 | 95.0 |
| Amrinone* | 0.1 | 9.0 |
|  | 1.0 | 80.0 |

*3-Amino-5-(4-pyridyl)-2(1H)—pyridinone; known compound actually used as cardiotonic medicine.

Test Method B (Anti-platelet activity):

Platelet rich plasma (PRP) which contains $6.5\text{–}7.5 \times 10^8$ platelet/ml was prepared from rabbit blood. To the 200 μl of PRP, 5 μl of calcium chloride (1 mM) and 50 μl of pH 7.4 Tris-acetate solution (5 mM) containing 120 mM NaCl and test compound were added successively, and then stirred for 2 min. at 37° C. To the solution, 5 μl of adenosine diphosphate (ADP) (2.5 μM) or collagen (2.5 μg/ml) was added as an aggregation inducer. Aggregation was measured by using an aggregometer (NKK HEMA TRACER 1). $ID_{50}$ is shown in Table 2.

Test Results B

TABLE 2

| Test Compound (Example No.) | $ID_{50}$ (Mol) ADP | Collagen |
|---|---|---|
| Example 48 | $2.4 \times 10^{-7}$ | $1.5 \times 10^{-7}$ |
| Example 57 | $3.0 \times 10^{-7}$ | $4.2 \times 10^{-7}$ |
| Example 58 | $3.4 \times 10^{-7}$ | $1.9 \times 10^{-7}$ |
| Example 59 | $3.6 \times 10^{-6}$ | $2.3 \times 10^{-7}$ |
| Example 72 | $7.9 \times 10^{-7}$ | $1.7 \times 10^{-7}$ |

Test Method C (Cerebrovescular vasodilative activity):

Mongrel dogs of either sex were anesthetized with sodium pentobarbital (35 mg/kg. i.p.). After the external carotid artery was ligated, a flowmeter probe was fitted to the common carotid artery. Polyethylene cannulas were inserted in the femoral artery for measurement of blood pressure and in the saphenous vein for injection of drug. Blood pressure was measured with a pressure transducer and the arterial pulse was also used to trigger a heart rate meter. Blood pressure, heart rate and cerebral blood flow (C.B.F.) were recorded on a polygraph.

Test compound was dissolved in an equimolar solution of hydrochloric acid and diluted with water (0.2 ml/kg), and injected intravenously. The prarmeters after dosing were compared with those during the predosing period.

Test Results C

Mean ratios of C.B.F. are shown in table 3.

TABLE 3

| Test Compound (Example No.) | Dose (mg/kg) | C. B. F. increase (%) |
|---|---|---|
| Example 48 | 0.01 | 40.0 |
|  | 0.1 | 57.0 |
| Example 55 | 0.1 | 38.0 |
|  | 1.0 | 77.0 |
| Example 56 | 0.1 | 50.0 |
|  | 1.0 | 52.0 |
| Example 57 | 0.01 | 59.0 |
|  | 0.1 | 57.0 |
| Example 72 | 0.1 | 35.0 |
|  | 1.0 | 59.0 |

Test Method D (Antihypertensive activity):

Five-week old male Wistar rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150–200 mmHg were used for experiment between 5 and 7 weeks after surgery.

The test compounds were administered orally. Blood pressure was measured at the femoral artery by means of a pressure transducer and recorded as electrically integrated values of mean arterial pressure.

Test Results D

Mean ratios of maximum decrease of blood pressure (mmHg) are shown in table 4.

TABLE 4

| Test Compound (Example No.) | Dose (mg/kg) | Effect Max (%) |
|---|---|---|
| Example 57 | 1.0 | 44.0 |
| Example 72 | 1.0 | 38.0 |

As being apparent from the above test results, the object compound [I] of the present invention are useful as cardiotonics, antihypertensive agents, cerebrovascular vasodilators and anti-platelet agents.

For therapeutic administration, the object compounds [I] of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral of external administration. The pharmaceutical preparation may be compounded in a solid form such as capsule, tablet, dragee or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 0.01 mg/kg to 500 mg/kg, 1 to 4 times a day. However, the above dosage may be increased or decreased according to age, weight, conditions of the patient or the administering method.

The following examples are given only for the purpose of illustrating the present invention in more detail.

EXAMPLE 1

To a mixture of ethyl veratroylacetate (45 g) and urea (11.7 g) were added conc. hydrochloric acid (5 drops) and ethanol (5 ml). The mixture was heated at 120° C. for 16 hours under reduced pressure. To the residue was added another conc. hydrochloric acid (5 drops) and ethanol (5 ml) and the mixture was heated again at 150° C. for 2 hours under reduced pressure. The resulting residue was washed successively with ethyl acetate, ethanol and isopropyl ether to give 6-(3,4-dimethoxyphenyl)-2,4(1H,3H)-pyrimidinedione (12.2 g).

mp: >300° C.

IR (Nujol): 1720, 1670 cm$^{-1}$

NMR (DMSO-d$_6$, δ): 11.0 (1H, br s), 7.4 (1H, d, J=9 Hz), 7.35 (1H, s), 7.05 (1H, d, J=9 Hz), 5.85 (1H, s), 5.4 (1H, br s), 3.86 (3H, s), 3.83 (3H, s).

EXAMPLE 2

To a mixture of ethyl veratroylacetate (10 g) and N,N'-dimethylurea (3.84 g) were added conc. hydrochloric acid (1 drop) and ethanol (1 ml). The mixture was heated at 120° C. for 3.5 hours under reduced pressure. To the residue was added another conc. hydrochloric acid (2 drops) and the mixture was heated again at 120° C. for 4 hours under reduced pressure. To the reaction mixture was added water and extracted with ethyl acetate. The extract was dried over magnesium sulfate and evaporated under reduced pressure. The residue was triturated with a mixture of isopropyl ether and ethyl acetate to give 6-(3,4-dimethoxyphenyl)-1,3-dimethyl-2,4(1H,3H)pyrimidinedione (7.60 g).

mp 118°–120° C.

IR (Nujol): 1700, 1660 cm$^{-1}$

NMR (DMSO-d$_6$, δ): 7.24 (1H, s), 7.20 (2H, s), 5.72 (1H, s), 3.90 (3H, s), 3.88 (3H, s), 3.28 (3H, s), 3.20 (3H, s).

EXAMPLE 3

1,3-Dimethyl-6-(4-methoxy-2-methylphenyl)-2,4(1H,3H)pyrimidinedione (4.8 g) was obtained according to substantially the same manner as that of Example 2 from ethyl 2-(4-methoxy-3-methylbenzyl)acetate (5.0 g) and N,N'-dimethylurea (2.05 g).

IR (film): 1700, 1660, 1615 cm$^{-1}$

NMR (CDCl$_3$, δ): 6.7–7.2 (3H, m), 5.62 (1H, s), 3.82 (3H, s), 3.40 (3H, s), 3.06 (3H, s), 2.20 (3H, s).

EXAMPLE 4

6-(3,4-Dichlorophenyl)-1,3-dimethyl-2,4(1H,3H)pyrimidinedione (5.27 g) was obtained according to substantially the same manner as that of Example 2 from ethyl 2-(3,4-dichlorobenzoyl)acetate (10.0 g) and N,N'-dimethylurea (3.71 g).

mp: 172°–175° C.

IR (Nujol): 1695, 1660, 1620 cm$^{-1}$

NMR (DMSO-d$_6$, δ): 7.83 (1H, d, J=2 Hz), 7.80 (1H, d, J=8 Hz), 7.50 (1H, dd, J=2 Hz, 8 Hz), 5.68 (1H, s), 3.23 (3H, s), 3.10 (3H, s).

EXAMPLE 5

1,3-Dimethyl-6-(2,3,4-trimethoxyphenyl)-2,4(1H,3H)pyrimidinedione (5.58 g) was obtained according to substantially the same manner as that of Example 2 from ethyl 2-(2,3,4-trimethoxybenzoyl)acetate (10.0 g) and N,N'-dimethylurea (3.75 g).

mp: 85°–87° C.

IR (Nujol): 1705, 1660 cm$^{-1}$

NMR (CDCl$_3$, δ): 6.86 (1H, d, J=8 Hz), 6.71 (1H, d, J=8 Hz), 5.66 (1H, s), 3.9 (6H, s), 3.85 (3H, s), 3.40 (3H, s), 3.16 (3H, s).

EXAMPLE 6

5-(3,4-Dimethoxyphenyl)-2,4(1H,3H)-pyrimidinedione (0.52 g) was obtained according to substantially the same manner as that of Example 2 from methyl 2-(3,4-dimethoxyphenyl)-2-formylacetate (1.2 g) and urea (0.3 g).

mp: 180°–185° C.

NMR (DMSO-d$_6$, δ): 3.73 (3H, s), 3.80 (3H, s), 4.40 (1H, br.s), 4.48 (1H, br.s), 6.60–7.15 (3H, m), 8.17 (1H, d, J=4 Hz).

EXAMPLE 7

5-(3,4-Dimethoxyphenyl)-1,3-dimethyl-2,4(1H,3H)pyrimidinedione (0.78 g) was obtained according to substantially the same manner as that of Example 2 from methyl 2-(3,4-dimethoxyphenyl)-2-formylacetate (1.2 g) and N,N'-dimethylurea (0.49 g).

mp: 146°–148° C.

IR (Nujol): 1685, 1650 cm$^{-1}$

NMR (DMSO-d$_6$, δ): 3.23 (3H, s), 3.37 (3H, s), 3.78 (6H, s), 6.85–7.20 (3H, m), 7.90 (1H, s).

EXAMPLE 8

To a solution of ethyl veratroylacetate (100 g) in toluene (1.0 l) was added N-methylurea (29.4 g) and the mixture was refluxed under azeotropic dehydration by use of Cope apparatus for one day. After cooling, the resultant precipitates were filtered. To the filtrate was added an additional N-methylurea (10.0 g) and the mixture was refluxed under the same condition for one day. After cooling, the resulting precipitates were filtered. The combined precipitates were washed successively with water and diisopropyl ether and dried under reduced pressure.

To a suspension of the precipitates obtained above in toluene (250 ml) was added conc.hydrochloric acid (1 ml), and the suspension was refluxed under azeotropic dehydration for 5.5 hours. The mixture was cooled, and the resulting precipitates were collected by filtration and recrystallized from a mixture of chloroform and methanol (9:1) to afford 6-(3,4-dimethoxyphenyl)-3-methyl-2,4(1H,3H)pyrimidinedione (24.9 g).

The filtrate was evaporated and the residue was recrystallized from chloroform to afford 6-(3,4-dimethoxyphenyl)-1-methyl-2,4(1H,3H)-pyrimidinedione (1.77 g).

(a) 6-(3,4-Dimethoxyphenyl)-3-methyl-2,4(1H,3H)-pyrimidinedione mp: 262°–263° C.

IR (Nujol): 1710, 1640, 1610 cm$^{-1}$

NMR (DMSO-d$_6$, δ): 11.3 (1H, brs), 6.9–7.6 (3H, m), 5.98 (1H, s), 3.84 (3H, s), 3.82 (3H, s), 3.17 (3H, s).

(b) 6-(3,4-Dimethoxyphenyl)-1-methyl-2,4(1H,3H)-pyrimidinedione mp: 266°–268° C.

IR (Nujol): 1690, 1660, 1620 cm$^{-1}$

NMR (DMSO-d$_6$, δ): 11.3 (1H, brs), 7.04 (3H, s), 5.46 (1H, s), 3.80 (6H, s), 3.07 (3H, s).

EXAMPLE 9

6-(4-Methoxyphenyl)-3-methyl-2,4(1H,3H)-pyrimidinedione (18.7 g) was obtained according to substantially the same manner as that of Example 8 from ethyl 2-(4-methoxybenzoyl)acetate (100 g) and N-methylurea (33.3 g).

mp: 239°–240° C.

IR (Nujol): 1730, 1705, 1625, 1600, 1570 cm$^{-1}$

NMR (DMSO-d$_6$, δ): 3.20 (3H, s), 3.84 (3H, s), 5.91 (1H, s), 7.04 (2H, d, J=9.0 Hz), 7.75 (2H, d, J=9.0 Hz), 11.18 (1H, br, s).

EXAMPLE 10

To a mixture of ethyl veratroylacetate (10 g) and N,N'-diethylurea (5.06 g) were added conc. hydrochloric acid (1 drop) and ethanol (1 ml). The mixture was heated at 120° C. for 3.5 hours under reduced pressure. To the residue was added another conc. hydrochloric acid (2 drops) and the mixture was heated again at 120° C. for 4 hours under reduced pressure. To the reaction mixture was added water and extracted with ethyl acetate. The extract was dried over magnesium sulfate and evaporated under reduced pressure. The residue was triturated with a mixture of diisopropyl ether and ethyl acetate to give 1,3-diethyl-6-(3,4-dimethoxyphenyl)-2,4(1H,3H)-pyrimidinedione (3.20 g).

mp: 104°–107° C.

IR (Nujol): 1690, 1650 cm$^{-1}$

NMR (DMSO-d$_6$, δ): 6.8–7.0 (3H, m), 5.63 (1H, s), 4.06 (2H, q, J=7 Hz), 3.93 (3H, s), 3.90 (3H, s), 3.78 (2H, q, J=7 Hz), 1.29 (3H, t, J=7 Hz), 1.15 (3H, t, J=7 Hz).

EXAMPLE 11

1,3-Dimethyl-6-(3,4,5-trimethoxyphenyl)-2,4(1H,3H)-pyrimidinedione (2.1 g) was obtained according to the substantially same manner as that of Example 10 from ethyl 2-(3,4,5-trimethoxybenzoyl)acetate (2.82 g) and N,N'-dimethylurea (0.97 g).

mp: 176°–177° C.

IR (Nujol): 1705, 1650 cm$^{-1}$

NMR (DMSO-d$_6$, δ): 3.17 (3H, s), 3.23 (3H, s), 3.73 (3H, s), 3.81 (6H, s), 5.67 (1H, s), 6.80 (2H, s).

EXAMPLE 12

To a mixture of ethyl nicotinoylacetate (2.30 g) and N,N'-dimethylurea (1.05 g) were added conc. hydrochloric acid (a few drops) and ethanol (1 ml) and the mixture was stirred at 110°–115° C. for 4 hours under reduced pressure (30 mmHg). After being cooled to ambient temperature, the solution was adjusted to pH 7.0 with an aqueous solution of sodium bicarbonate and extracted with ethyl acetate. The extract was washed with brine, dried over magnesium sulfate and evaporated to give 6-(3-pyridyl)-1,3-dimethyl-2,4(1H,3H)-pyrimidinedione (0.91 g).

mp: 120°–122° C.

IR (Nujol): 1705, 1660 cm$^{-1}$

NMR (DMSO-d$_6$, δ): 8.68 (2H, m), 7.95 (1H, m), 7.53 (1H, dd, J=4.5 Hz), 5.70 (1H, s), 3.23 (3H, s), 3.10 (3H, s).

EXAMPLE 13

To a solution of ethyl veratroylacetate (8.0 g) in tetralin (24 ml) was added N-methylurea (3.52 g) and the mixture was heated for an hour at 170° C. After being cooled to 95° C., ethyl acetate (33 ml) was added thereto. The precipitate was collected by filtration and washed with ethyl acetate to give 6-(3,4-dimethoxyphenyl)-3-methyl-2,4(1H,3H)-pyrimidinedione (3.35 g).

IR (Nujol): 1710, 1640, 1610 cm$^{-1}$

EXAMPLE 14

To a solution of 6-(3,4-dimethoxyphenyl)-2,4(1H,3H)-pyrimidinedione (8.0 g) in N,N-dimethylformamide (50 ml) and added sodium hydride (50% in oil, 3.40 g) and the mixture was heated at 60° C. for 30 minutes with stirring. To this mixture which was cooled to ambient temperature was added methyl iodide (40 ml) and the resulting mixture was stirred at the same temperature for 90 minutes. To the reaction mixture was added water and evaporated under reduced pressure. The residue was diluted with water (300 ml) and extracted with ethyl acetate. The extract was washed with water, dried over magnesium sulfate and evaporated under reduced pressure. The residue was subjected to column chromatography on silica gel and eluted with a mixture of chloroform and methanol. The fractions containing the object compound were combined and concentrated under reduced pressure to give 6-(3,4-dimethoxyphenyl)-1,3-dimethyl-2,4(1H,3H)-pyrimidinedione (1.94 g).

mp: 118°–120° C.

IR (Nujol): 1700, 1660 cm$^{-1}$

NMR (DMSO-d$_6$, δ): 7.24 (1H, s), 7.20 (2H, s), 5.72 (1H, s), 3.90 (3H, s), 3.88 (3H, s), 3.28 (3H, s), 3.20 (3H, s).

EXAMPLE 15

To a suspension of 6-(3,4-dimethoxyphenyl)-2,4(1H,3H)-pyrimidinedione (1.0 g) in a mixture of water (5 ml) and methanol (5 ml) was added potassium hydroxide (0.57 g), and to an almost dissolved mixture was added methyl iodide (5 ml). The mixture was stirred at ambient temperature for 18 hours. The resulting precipitates were filtered and washed successively with water, ethanol and diisopropyl ether to afford 6-(3,4-dimethoxyphenyl)-3-methyl-2,4(1H,3H)-pyrimidinedione (0.13 g).

mp: 262°–263° C.

EXAMPLE 16

To a solution of 6-(3,4-dimethoxyphenyl)-3-methyl-2,4(1H,3H)-pyrimidinedione (3.0 g) in N,N-dimethylformamide (30 ml) was added sodium hydride (60% in oil, 0.5 g). The mixture was heated at 60° C. with stirring for 20 minutes and cooled to 0° C. To the mixture was added n-propyl iodide (15 ml) with stirring, which was continued at 0° C. for 2 hours and at ambient temperature for 3 hours. After addition of water, the reaction mixture was extracted with ethyl acetate. The organic extract was washed with water, dried over magnesium sulfate and evaporated under reduced pressure. The residue was triturated with diisopropyl ether and the resulting precipitates were collected by filtration to give 6-(3,4-dimethoxyphenyl)-3-methyl-2-propoxy-4(3H)-pyrimidinone (1.15 g) as by-product.

The filtrate was evaporated to give crystal, which was collected by filtration to give 6-(3,4-dimethoxyphenyl)-3-methyl-1-propyl-2,4(1H,3H)-pyrimidinedione (0.94 g).

(a) 6-(3,4-dimethoxyphenyl)-3-methyl-2-propoxy-4(3H)-pyrimidinone mp: 131°–133° C.

IR (Nujol): 1670, 1600 cm$^{-1}$

NMR (CDCl$_3$, δ): 7.57 (1H, dd, J=2 Hz, J=8 Hz), 7.50 (1H, d, J=2 Hz), 6.90 (1H, d, J=8 Hz), 6.50 (1H, s), 4.48 (2H, t, J=7 Hz), 3.92 (6H, s), 3.43 (3H, s), 1.91 (2H, tq, J=7 Hz, 7 Hz), 1.06 (3H, t, J=7 Hz).

(b) 6-(3,4-dimethoxyphenyl)-3-methyl-1-propyl-2,4(1H,3H)-pyrimidinedione mp: 103°–105° C.

IR (Nujol): 1705, 1660 cm$^{-1}$

NMR (CDCl$_3$, δ): 6.75–7.0 (3H, m), 5.64 (1H, s), 3.93 (6H, s), 3.5–3.9 (2H, m), 3.37 (3H, s), 1.20–1.90 (2H, m), 0.74 (3H, t, J=7 Hz).

EXAMPLE 17

To a solution of 6-(3,4-dimethoxyphenyl)-3-methyl-2,4(1H,3H)-pyrimidinedione (1.0 g) in N,N-dimethylformamide (10 ml) was added sodium hydride (60% in oil, 0.17 g). The mixture was heated at 60° C. with stirring for 20 minutes and cooled to ambient temperature. To the mixture was added ethyl iodide (5 ml) with stirring, which was continued at ambient temperature for 3.5 hours. To the reaction mixture was added water, and extracted with ethyl acetate. The organic extract was washed with water, dried over magnesium sulfate and evaporated under reduced pressure. The residue was triturated with a mixture of ethyl acetate and diisopropyl ether and the resulting precipitates were collected by filtration to give 6-(3,4-dimethoxyphenyl)-2-ethoxy-3-methyl-4(3H)-pyrimidinone (0.18 g) as by-product.

mp: 137°–139° C.

IR (Nujol): 1675, 1600 cm$^{-1}$

NMR (DMSO-d$_6$, δ): 7.65 (1H, d, J=8 Hz), 7.58 (1H, s), 7.03 (1H, d, J=8 Hz), 6.62 (1H, s), 4.55 (2H, q, J=7 Hz), 3.82 (6H, s), 3.27 (3H, s), 1.41 (3H, t, J=7 Hz).

The filtrate was evaporated to dryness, and the residue was cooled to −10° C. and triturated with a mixture of ethyl acetate and diisopropyl ether to give 6-(3,4-dimethoxyphenyl)-1-ethyl-3-methyl-2,4(1H,3H)-pyrimidinedione (0.8 g); mp 110°–120° C. Thus obtained compound was recrystallized from a mixture of ethyl acetate and diisopropyl ether to give the desired compound as crystals. mp 111°–114° C.

IR (Nujol): 1695, 1655 cm$^{-1}$

NMR (DMSO-d$_6$, δ): 7.06 (3H, s), 5.56 (1H, s), 3.82 (6H, s), 3.69 (2H, q, J=6.5 Hz), 3.21 (3H, s), 1.05 (3H, t, J=6.5 Hz).

EXAMPLE 18

6-(3,4-Dimethoxyphenyl)-1-(2,3-epoxypropyl)-3-methyl-2,4(1H,3H)-pyrimidinedione (4.02 g) was obtained according to substantially the same manner as that of Example 17 from 6-(3,4-dimethoxyphenyl)-3-methyl-2,4(1H,3H)-pyrimidinedione (6.9 g), sodium hydride (60% in oil, 1.16 g) and epichlorohydrin (30 ml).

mp: 98°–103° C. [recrystallization from a mixture of ethyl acetate and diisopropyl ether (1:1 V/V)]

IR (Nujol): 1700, 1660 cm$^{-1}$

NMR (CDCl$_3$, δ): 6.93 (3H, s), 5.68 (1H, s), 3.93 (6H, s), 3.7–4.1 (2H, m), 3.4 (3H, s), 3.1–3.6 (1H, m), 2.77 (1H, t, J=4.5 Hz), 2.40 (1H, dd, J=4.5 Hz, J=3 Hz).

EXAMPLE 19

1-Allyl-6-(3,4-dimethoxyphenyl)-3-methyl-2,4(1H,3H)-pyrimidinedione (2.66 g) was obtained according to substantially the same manner as that of Example 17 from 6-(3,4-dimethoxyphenyl)-3-methyl-2,4(1H,3H)-pyrimidinedione (3.0 g), sodium hydride (50% in oil, 0.6 g) and allyl bromide.

mp: 88°–92° C.

IR (Nujol): 1700, 1660, 1620, 1590 cm$^{-1}$

NMR (DMSO-d$_6$, δ): 3.24 (3H, s), 3.77 (3H, s), 3.81 (3H, s), 4.27 (2H, m), 5.11 (2H, m), 5.50–6.14 (1H, m), 5.61 (1H, s), 7.02 (3H, s).

EXAMPLE 20

1-Benzyl-6-(3,4-dimethoxyphenyl)-3-methyl-2,4(1H,3H)-pyrimidinedione (3.4 g) was obtained according to substantially the same manner as that of Example 17 from 6-(3,4-dimethoxyphenyl)-3-methyl-2,4(1H,3H)-pyrimidinedione (3.0g), sodium hydride (50% in oil, 0.6 g) and benzyl bromide (6.8 ml).

mp: 87°–95° C.

IR (Nujol): 1700, 1660, 1615, 1685 cm$^{-1}$

NMR (DMSO-d$_6$, δ): 3.27 (3H, s), 3.48 (3H, s), 3.76 (3H, s), 4.92 (2H, s), 5.67 (1H, s), 6.74–7.70 (8H, m).

EXAMPLE 21

1,3-Dimethyl-6-(4-methoxyphenyl)-2,4(1H,3H)-pyrimidinedione (3.1 g) was obtained according to substantially the same manner as that of Example 17 from 6-(4-methoxyphenyl)-3-methyl-2,4(1H,3H)-pyrimidinedione (5.0 g), sodium hydride (50% in oil, 1.1 g) and methyl iodide (6.7 ml).

mp: 76°–79° C.

IR (Nujol): 1690, 1655, 1610 cm$^{-1}$

NMR (DMSO-d$_6$, δ): 3.17 (3H, s), 3.26 (3H, s), 3.87 (3H, s), 5.62 (1H, s), 7.07 (2H, d, J=9.0 Hz), 7.50 (2H, d, J=9.0 Hz).

EXAMPLE 22

To a suspension of 3,4-dihydro-6-(3,4-dimethoxyphenyl)-3-methyl-4-(2,4,6-trimethylphenylimino)-2(1H)-pyrimidinone (0.63 g) in N,N-dimethylformamide (15 ml) were added potassium hydroxide (0.16 g) and ethyl iodide (0.66 ml) and the mixture was stirred at ambient temperature for 4 hours. The mixture was poured into water (100 ml), and was extracted with chloroform. The extract was washed with water, dried over magnesium sulfate, and evaporated under reduced pressure. The residue was chromatographed on silica gel eluting with chloroform to give 3,4-dihydro-6-(3,4-dimethoxyphenyl)-1-ethyl-3-methyl-4-(2,4,6-trimethylphenylimino)-2(1H)-pyrimidinone (0.39 g).

mp: 112°–114° C.

IR (Nujol): 1685, 1660, 1600 cm$^{-1}$

NMR (CDCl$_3$, δ): 6.6–6.9 (5H, m), 5.07 (1H, s), 3.85 (3H, s), 3.83 (3H, s), 3.80 (2H, q, J=7 Hz), 3.57 (3H, s), 2.20 (3H, s), 2.02 (6H, s), 1.12 (3H, t, J=7 Hz).

The compound obtained above was recrystallized from a mixture of ethanol and water (3:1) to give the desired compound as a crystal. mp 116°–118° C.

EXAMPLE 23

To a mixture of 3,4-dihydro-6-(3,4-dimethoxyphenyl)-3-methyl-4-(2,4,6-trimethylphenylimino)-2(1H)-pyrimidinone (2.73 g) and potassium tert-butoxide (1.0 g) in dimethylformamide (27 ml) was added ethyl iodide (1.2 ml) and mixture was stirred for 3 hours. Then another potassium tert-butoxide (1.1 g) and ethyl iodide (0.57 ml) were added. The mixture was stirred for more 2 hours and poured into water. The precipitate was collected by filtration and added to 1N hydrochloric acid (15 ml). The mixture was refluxed for 5 hours. After being cooled, the reaction mixture was adjusted to pH 8.5 with aqueous sodium hydroxide. The precipitate was collected by filtration and added to diisopropyl ether (50 ml). The resultant mixture was filtered and the filtrate was evaporated in vacuo. The residue was recrystallized from a mixture of ethanol and water (3:1) to give 3,4-dihydro-6-(3,4-dimethoxyphenyl)-1-ethyl-3-methyl-4-(2,4,6-tri-methylphenylimino)-2(1H)-pyrimidinone (1.6 g). mp 116°–118° C.

IR (Nujol): 1685, 1660, 1600 cm$^{-1}$

NMR (CDCl$_3$, $\delta$): 6.6–6.9 (5H, m), 5.07 (1H, s), 3.85 (3H, s), 3.83 (3H, s), 3.80 (2H, q, J=7 Hz), 3.57 (3H, s), 2.20 (3H, s), 2.02 (6H, s), 1.12 (3H, t, J=7 Hz).

EXAMPLE 24

To a suspension of 3,4-dihydro-6-(3,4-dimethoxyphenyl)-3-methyl-4-(2,4,6-trimethylphenylimino)-2(1H)-pyrimidinone (1.0 g) in N,N-dimethylformamide (10 ml) were added potassium tert-butoxide (0.38 g) and methyl iodide (0.33 ml) and the mixture was stirred at ambient temperature for 5 hours. To the reaction mixture were added additional potassium tertbutoxide (0.38 g) and methyl iodide (0.17 ml) and the mixture was stirred at ambient temperature for more 2 hours. The mixture was poured into water (100 ml) and the resulting precipitates were collected by filtration. The precipitate was recrystallized from a mixture of methanol and water (5:1) to give 3,4-dihydro-6-(3,4-dimethoxyphenyl)-1,3-dimethyl-4-(2,4,6-trimethylphenylimino)-2(1H)-pyrimidinone (0.83 g).

mp 96°–98° C.

IR (Nujol): 1685, 1640, 1590 cm$^{-1}$

NMR (CDCl$_3$, $\delta$): 6.8(4H, s), 6.7(1H, s), 5.13(1H, s), 3.87(3H, s), 3.85(3H, s), 3.57(3H, s), 3.14(3H, s), 2.20(3H, s), 2.00(6H, s).

EXAMPLE 25

To a mixture of 3,4-dihydro-6-(3,4-dimethoxyphenyl)-1-methyl-4-(2,4,6-trimethylphenylimino)-2(1H)-pyrimidinone (300 mg) and potassium tert-butoxide (0.12 g) in N,N-dimethylformamide (10 ml) was added methyl iodide (0.1 ml).

The mixture was stirred at ambient temperature for 2 hours, and then the reaction mixture was poured into water (150 ml). The precipitates were collected by filtration and recrystallized from a mixture of methanol and water (5:1) to give 3,4-dihydro-6-(3,4-dimethoxyphenyl)-1,3-dimethyl-4-(2,4,6-trimethylphenylimino)-2(1H)-pyrimidinone (90 mg).

mp 96°–98° C.

IR (Nujol): 1685, 1640, 1590 cm$^{-1}$

NMR (CDCl$_3$, $\delta$): 6.8(4H, s), 6.7(1H, s), 5.13(1H, s), 3.87(3H, s), 3.85(3H, s), 3.57(3H, s), 3.14(3H, s), 2.20(3H, s), 2.00(6H, s).

EXAMPLE 26

To a solution of 6-(3,4-dimethoxyphenyl)-3-methyl-2,4(1H,3H)-pyrimidinedione (3.0 g) in N,N-dimethylformamide (30 ml) was added sodium hydride (60% oil suspension, 0.50 g). The mixture was heated at 60° C. with stirring for 20 minutes and cooled to ambient temperature. To the mixture was added isopropyl bromide (15 ml) with stirring, which was continued at ambient temperature for 5 hours, and at 50° C. for 25 hours. To the reaction mixture was added water, and extracted with ethyl acetate. The organic extract was washed with water, dried over magnesium sulfate and evaporated under reduced pressure. The residue was triturated in diisopropyl ether to give 6-(3,4-dimethoxyphenyl)-2-isopropoxy-3-methyl-4(3H)-pyrimidinone (2.73 g).

mp: 124°–126° C.

IR (Nujol): 1680, 1670, 1600 cm$^{-1}$

NMR (DMSO-d$_6$, $\delta$): 7.5–7.8 (2H, m), 7.01 (1H, d, J=8 Hz), 5.4 (1H, sep. J=6 Hz), 3.83 (6H, s), 3.27 (3H, s), 1.42 (6H, d, J=6 Hz).

EXAMPLE 27

To a suspension of 3,4-dihydro-6-(3,4-dimethoxyphenyl)-3-methyl-4-(2,4,6-trimethylphenylimino)-2-(1H)pyrimidione (1.42 g) in N,N-dimethylformamide (1.42 ml) were added potassium hydroxide (5.5 g) and ethyl iodide (6.0 ml) and the mixture was stirred at ambient temperature for 2.5 hours. To the reaction mixture were added additional potassium tert-butoxide (5.0 g) and ethyl iodide (3.0 ml) and the mixture was stirred at ambient temperature for more 2 hours. The mixture was poured into ice-water (150 ml). The resulting precipitates were collected by filtration, air-dried and subjected to column chromatography on silica gel using a mixture of dichloromethane and methanol as an eluent to give 3,4-dihydro-6-(3,4-dimethoxyphenyl)-2-ethoxy-3-methyl-4-(2,4,6-trimethylphenylimino)pyrimidine (0.135 g).

mp 116°–119° C.

IR (Nujol): 1640, 1650, 1590 cm$^{-1}$

NMR (CDCl$_3$, $\delta$): 7.15–7.55 (2H, m), 6.7–7.0 (3H, m), 5.83 (1H, s), 4.56 (2H, q, J=7 Hz), 3.85 (6H, s), 3.56 (3H, s), 2.25 (3H, s), 2.04 (6H, s), 1.13 (3H, t, J=7 Hz).

The other fractions were combined and evaporated in vacuo. The residue was recrystallized from a mixture of ethanol and water (4:1) to give 3,4-dihydro-6-(3,4-dimethoxyphenyl)-1-ethyl-3-methyl-4-(2,4,6-trimethylphenylimino)-2(1H)-pyrimidinone (1.6 g).

mp 116°–118° C.

IR (Nujol): 1685, 1660, 1600 cm$^{-1}$

NMR (CDCl$_3$, $\delta$): 6.6–6.9 (5H, m), 5.07 (1H, s), 3.85 (3H, s), 3.83 (3H, s), 3.80 (2H, q, J=7 Hz), 3.57 (3H, s), 2.20 (3H, s), 2.02 (6H, s), 1.12 (3H, t, J=7 Hz).

EXAMPLE 28

To a solution of 6-(3,4-dimethoxyphenyl)-1-(2,3-epoxypropyl)-3-methyl-2,4(1H,3H)-pyrimidinedione (0.6 g) in ehtanol (20 ml) was added tert-butylamine (2 ml). The mixture was refluxed for 2.5 hours and evaporated in vacuo. The resulting syrup was triturated in a mixture of diethyl ether and diisopropyl ether to give 1-(3-tert-butylamino-2-hydroxy-1-propyl)-6-(3,4-dimethoxyphenyl)-3-methyl-2,4(1H,3H)pyrimidinedione (0.66 g).

mp: 123°–125° C.

IR (Nujol): 1700, 1655 cm$^{-1}$

NMR (CDCl$_3$, δ): 6.93 (3H, br. s), 5.68 (1H, s), 3.92 (3H, s), 3.88 (3H, s), 3.77 (2H, br. s), 3.7–4.0 (1H, m), 3.37 (3H, s), 2.1–2.8 (2H, m), 2.0 (2H, br. s), 1.00 (9H, s).

EXAMPLE 29

A mixture of 6-(3,4-dimethoxyphenyl)-1,3-dimethyl-2,4(1H,3H)-pyrimidinedione (1.57 g) and phosphorus pentasulfide (3.3 g) in pyridine was refluxed for 15 hours with stirring. The reaction mixture was evaporated under reduced pressure. The residue was washed with 1N-hydrochloric acid and extracted with dichloromethane. The extract was washed with water, dried over magnesium sulfate and evaporated under reduced pressure. The residue was triturated in diisopropyl ether to give 3,4-dihydro-6-(3,4-dimethoxyphenyl)-1,3-dimethyl-4-thioxo-2(1H)-pyrimidinone (1.58 g).

mp: 146°–148° C.

IR (Nujol): 1685, 1615 cm$^{-1}$

NMR (CDCl$_3$, δ): 6.95 (2H, s), 6.86 (1H, s), 6.60 (1H, s), 3.93 (3H, s), 3.90 (3H, s), 3.84 (3H, s), 3.30 (3H, s).

EXAMPLE 30

3,4-Dihydro-1,3-dimethyl-6-phenyl-4-thioxo-2(1H)-pyrimidinone (3.0 g) was obtained according to the substantially same manner as that of Example 29 from 1,3-dimethyl-6-phenyl-2,4(1H,3H)-pyrimidinedione (4.0 g) and phosphorus pentasulfide (4.7 g).

mp: 101°–103° C.

IR (Nujol): 1680, 1615 cm$^{-1}$

NMR (DMSO-d$_6$, δ): 7.53 (5H, s), 6.44 (1H, s), 3.68 (3H, s), 3.15 (3H, s).

EXAMPLE 31

3,4-Dihydro-1,3-dimethyl-6-(3-pyridyl)-4-thioxo-2(1H)-pyrimidinone (0.69 g) was obtained according to the substantially same manner as that of Example 29 from 1,3-dimethyl-6-(3-Pyridyl)-2,4(1H,3H)-pyrimidinedione (0.78 g) and phosphorus pentasulfide (0.92 g).

mp: 136°–139° C.

IR (Nujol): 1680, 1650, 1615 cm$^{-1}$

NMR (DMSO-d$_6$, δ): 8.87 (2H, m), 8.03 (1H, m), 7.58 (1H, dd, J=4.5 Hz), 6.54 (1H, s), 3.71 (3H, s), 3.18 (3H, s).

EXAMPLE 32

3,4-Dihydro-1,3-dimethyl-6-(4-methoxy-2-methylphenyl)-4-thioxo-2(1H)-pyrimidinone (3.51 g) was obtained according to substantially the same manner as that of Example 29 from 1,3-dimethyl-6-(4-methoxy-2-methylphenyl)-2,4(1H,3H)pyrimidinedione (4.80 g) and phosphorus pentasulfide (8.17 g).

mp: 117°–119° C.

IR (Nujol): 1690, 1610 cm$^{-1}$

NMR (CDCl$_3$, δ): 6.6–7.3 (3H, m), 6.55 (1H, s), 3.84 (6H, s), 3.12 (3H, s), 2.22 (3H, s).

EXAMPLE 33

3,4-Dihydro-6-(3,4-dichlorophenyl)-1,3-dimethyl-4-thioxo-2(1H)-pyrimidinone (4.57 g) was obtained according to substantially the same manner as that of Example 29 from 6-(3,4-dichlorophenyl)-1,3-dimethyl-2,4(1H,3H)-pyrimidinedione (5.20 g) and phosphorus pentasulfide (10.0 g).

mp: 126°–127° C.

IR (Nujol): 1690, 1620, 1100 cm$^{-1}$

NMR (DMSO-d$_6$, δ): 7.85 (1H, d, J=2 Hz), 7.80 (1H, d, J=8 Hz), 7.52 (1H, dd, J=2 Hz, 8 Hz), 6.50 (1H, s), 3.68 (3H, s), 3.14 (3H, s).

EXAMPLE 34

3,4-Dihydro-1,3-dimethyl-4-thioxo-6-(2,3,4-trimethoxyphenyl)-2(1H)-pyrimidinone (4.13 g) was obtained according to substantially the same manner as that of Example 29 from 1,3-dimethyl-6-(2,3,4-trimethoxyphenyl)-2,4(1H,3H)-pyrimidinedione (5.0 g) and phosphorus pentasulfide (7.25 g).

mp: 135°–137° C.

IR (Nujol): 1710, 1690, 1610 cm$^{-1}$

NMR (CDCl$_3$, δ): 6.87 (1H, d, J=9 Hz), 6.73 (1H, d, J=9 Hz), 6.57 (1H, s), 3.88 (6H, s), 3.84 (3H, s), 3.82 (3H, s), 3.18 (3H, s).

EXAMPLE 35

3,4-Dihydro-1,3-dimethyl-6-(4-methoxyphenyl)-4-thioxo-2(1H)-pyrimidinone (2.4 g) was obtained according to substantially the same manner as that of Example 29 from 1,3-dimethyl-6-(4-methoxyphenyl)-2,4(1H,3H)-pyrimidinedione (3.0 g) and phosphorus pentasulfide (8.1 g).

mp: 119°–121° C.

IR (Nujol): 1690, 1600 cm$^{-1}$

NMR (DMSO-d$_6$, δ): 3.20 (3H, s), 3.69 (3H, s), 3.84 (3H, s), 6.44 (1H, s), 7.08 (2H, d, J=9.0 Hz), 7.49 (2H, d, J=9.0 Hz).

EXAMPLE 36

3,4-Dihydro-6-(3,4-dimethoxyphenyl)-3-methyl-4-thioxo-2(1H)-pyrimidinone (1.95 g) was obtained according to substantially the same manner as that of Example 29 from 6-(3,4-dimethoxyphenyl)-3-methyl-2,4(1H,3H)-pyrimidinedione (2.0 g) and phosphorus pentasulfide (3.39 g).

mp 243°–248° C. (amorphous) [mp 247°–249° C.: crystal(recrystallization from ethanol)]

IR (Nujol): 1685, 1610 cm$^{-1}$

NMR (DMSO-d$_6$, δ): 8.6–9.0 (1H, br,s), 7.3–7.6 (2H, m), 7.06 (1H, d, J=9 Hz), 6.88 (1H, s), 3.86 (3H, s), 3.83 (3H, s), 3.63 (3H, s).

EXAMPLE 37

3,4-Dihydro-6-(3,4-dimethoxyphenyl)-3-methyl-1-propyl-4-thioxo-2(1H)-pyrimidinone (1.86 g) was obtained according to substantially the same manner as that of Example 29 from 6-(3,4-dimethoxyphenyl)-3-methyl-1-propyl-2,4(1H,3H)-pyrimidinedione (2.23 g) and phosphorus pentasulfide (3.26 g).

mp: 115°–120° C.

IR (Nujol): 1680, 1620 cm$^{-1}$

NMR (CDCl$_3$, δ): 6.8–7.0 (3H, m), 6.57 (1H, s), 3.93 (3H, s), 3.89 (3H, s), 3.83 (3H, s), 3.6–4.0 (2H, m), 1.4–1.9 (2H, m), 1.76 (3H, t, J=8 Hz).

EXAMPLE 38

1-Allyl-3,4-dihydro-6-(3,4-dimethoxyphenyl)-3-methyl-4-thioxo-2(1H)-pyrimidinone (2.0 g) was obtained according to substantially the same manner as that of Example 29 from 1-allyl-6-(3,4-dimethoxyphenyl)-3-methyl-2,4(1H,3H)-pyrimidinedione (2.5 g) and phosphorus pentasulfide (5.5 g).

mp: 103°–107° C.

IR (Nujol): 1680, 1615, 1600, 1580 cm$^{-1}$

NMR (DMSO-d$_6$, δ): 3.67 (3H, s), 3.75 (3H, s), 3.80 (3H, s), 4.29 (2H, m), 5.14 (2H, m), 5.52–6.26 (1H, m), 6.44 (1H, s), 7.03 (3H, s).

EXAMPLE 39

1-Benzyl-3,4-dihydro-6-(3,4-dimethoxyphenyl)-3-methyl-4-thioxo-2(1H)-pyrimidinone (2.9 g) was obtained according to substantially the same manner as that of Example 29 from 1-benzyl-6-(3,4-dimethoxyphenyl)-3-methyl-2,4(1H,3H)-pyrimidinedione (3.2 g) and phosphorus pentasulfide (6.1 g).

mp: 134°–139° C.

IR (Nujol): 1700, 1605, 1575 cm$^{-1}$

NMR (DMSO-d$_6$, δ): 3.48 (3H, s), 3.70 (3H, s), 3.76 (3H, s), 4.94 (2H, s), 6.49 (1H, s), 6.79–7.46 (8H, m).

EXAMPLE 40

3,4-Dihydro-5-(3,4-dimethoxyphenyl)-1,3-dimethyl-4-thioxo-2(1H)-pyrimidinone (2.45 g) was obtained according to substantially the same manner as that of Example 29 from 5-(3,4dimethoxyphenyl)-1,3-dimethyl-2,4(1H,3H)-pyrimidinedione (3.0 g) and phosphorus pentasulfide (2.78 g).

mp: 164°–165° C.

IR (Nujol): 1700, 1620 cm$^{-1}$

NMR (DMSO-d$_6$, δ): 3.38 (3H, s), 3.68 (3H, s), 3.72 (3H, s), 3.78 (3H, s), 6.90–7.10 (3H, m), 7.78 (1H, s).

EXAMPLE 41

3,4-Dihydro-6-(3,4-dimethoxyphenyl)-1-methyl-4-thioxo-2(1H)-pyrimidinone (2.42 g) was obtained according to substantially the same manner as that of Example 29 from 6-(3,4-dimethoxyphenyl)-1-methyl-2,4(1H, 3H)-pyrimidinedione (3.5 g) and phosphorus pentasulfide (3.0 g).

mp 192°–195° C.

IR (Nujol): 1690, 1600 cm$^{-1}$

NMR (CDCl$_3$, δ): 10.65 (1H, br, s), 6.8–7.1 (3H, m), 6.42 (1H, s), 3.90 (6H, s), 3.27 (3H, s).

EXAMPLE 42

3,4-Dihydro-6-(3,4-dimethoxyphenyl)-4-thioxo-2(1H)-pyrimidinone (0.63 g) was obtained according to substantially the same manner as that of Example 29 from 6-(3,4-dimethoxyphenyl)-2,4(1H,3H)-pyrimidinedione (1.09 g) and phosphorus pentasulfide (1.00 g).

mp 285°–288° C.

IR (Nujol): 1720, 1610, 1140 cm$^{-1}$

NMR (DMSO-d$_6$, δ): 12.12 (1H, brs), 11.40 (1H, brs), 7.1 (2H, m), 6.91 (1H, d, J=7 Hz), 6.49 (1H, s), 3.77 (3H, s), 3.74 (3H, s).

EXAMPLE 43

A mixture of 6-(3,4-dimethoxyphenyl)-1-ethyl-3-methyl-2,4(1H,3H)-pyrimidinedione (0.80 g) and phosphorus pentasulfide (1.8 g) in pyridine (18 ml) was refluxed for 15 hours with stirring. The reaction mixture was evaporated under reduced pressure. The residue was washed with 1N-hydrochloric acid and extracted with dichloromethane. The extract was washed with water, dried over magnesium sulfate and evaporated under reduced pressure. The residue was triturated in diisopropyl ether to give 3,4-dihydro-6-(3,4-dimethoxyphenyl)-1-ethyl-3-methyl-4-thioxo-2(1H)-pyrimidinone (0.60 g).

mp: 147°–150° C.

IR (Nujol): 1685, 1615 cm$^{-1}$

NMR (CDCl$_3$, δ): 6.8–7.0 (3H, m), 6.57 (1H, s), 3.93 (3H, s), 3.90 (3H, s), 3.83 (3H, s), 3.85 (2H, q, J=7 Hz), 1.18 (3H, t, J=7 Hz).

EXAMPLE 44

1,3-Diethyl-3,4-dihydro-6-(3,4-dimethoxyphenyl)-4-thioxo-2(1H)-pyrimidinone (1.74 g) was obtained according to the substantially same manner as that of Example 43 from 1,3-diethyl-6-(3,4-dimethoxyphenyl)-2,4(1H,3H)-pyrimidinedione (2.0 g) and phosphorus pentasulfide (4.0 g).

mp: 161°–164° C.

IR (Nujol): 1680, 1620, 1600 cm$^{-1}$

NMR (CDCl$_3$, δ): 6.8–7.0 (3H, m), 6.52 (1H, s), 4.60 (2H, q, J=7 Hz), 3.79 (2H, q, J=7 Hz), 3.93 (3H, s), 3.89 (3H, s), 1.36 (3H, t, J=7 Hz), 1.18 (3H, t, J=7 Hz).

EXAMPLE 45

3,4-Dihydro-1,3-dimethyl-6-(3,4,5-trimethoxyphenyl)-4-thioxo-2(1H)-pyrimidinone (0.65 g) was obtained according to the substantially same manner as that of Example 43 from 1,3-dimethyl-6-(3,4,5-trimethoxyphenyl)-2,4(1H,3H)-pyrimidinedione (0.72 g) and phosphorus pentasulfide (0.60 g).

mp: 165°–166° C.

IR (Nujol): 1685, 1120 cm$^{-1}$

NMR (DMSO-d$_6$, δ): 3.20 (3H, s), 3.68 (3H, s), 3.73 (3H, s), 3.82 (6H, s), 6.51 (1H, s), 6.84 (2H, s).

EXAMPLE 46

A mixture of 6-(3,4-dimethoxyphenyl)-2-isopropoxy-3-methyl-4(3H)-pyrimidinone (2.5 g) and phosphorus pentasulfide (3.5 g) in pyridine (50 ml) was refluxed for 13 hours with stirring. The reaction mixture was evaporated under reduced pressure. The residue was washed with 1N-hydrochloric acid and extracted with chloroform. The extract was washed with water, dried over magnesium sulfate and evaporated under reduced pressure. The residue was triturated in ethanol and the resulting precipitate was triturated again in chloroform and collected by filtration to give 3,4-dihydro-6-(3,4-dimethoxyphenyl)-3-methyl-4-thioxo-2(1H)-pyrimidinone (0.27 g).

The filtrate was evaporated under reduced pressure. The residue was triturated with diisopropyl ether to give 3,4-dihydro-6-(3,4-dimethoxyphenyl)-2-isopropoxy-3-methyl-4-thioxopyrimidine (0.88 g).

(a) 3,4-Dihydro-6-(3,4-dimethoxyphenyl)-2-isopropoxy-3-methyl-4-thioxopyrimidine.

mp: 128°–131° C.

IR (Nujol): 1600, 1580 cm$^{-1}$

NMR (CDCl$_3$, δ): 7.64 (1H, dd, J=2 Hz, J=9 Hz), 7.57 (1H, s), 7.48 (1H, d, J=2 Hz), 6.91 (1H, d, J=9 Hz), 5.48 (1H, sep. J=6 Hz), 3.90 (6H, s), 3.86 (3H, s), 1.46 (6H, d, J=6 Hz).

(b) 3,4-Dihydro-6-(3,4-dimethoxyphenyl)-3-methyl-4-thioxo-2(1H)-pyrimidinone.

mp: 245°–248° C.

IR (Nujol): 1685, 1610 cm$^{-1}$

EXAMPLE 47

To a suspension of 6-(3,4-dimethoxyphenyl)-3-methyl-2,4(1H,3H)-pyrimidinedione (1.5 g) in dioxane (15 ml) was added phosphorus pentasulfide (1.27 g) and the mixture was refluxed for 2 hours. After being cooled, ethanol (15 ml) was added thereto, and the mixture was refluxed for 2 hours again. After being cooled, the resulting precipitates were collected by filtration and washed successively with ethanol and diisopropyl ether to give 3,4-dihydro-6-(3,4-dimethoxyphenyl)-3-methyl-4-thioxo-2(1H)-pyrimidinone (0.85 g).

EXAMPLE 48

To a solution of 3,4-dihydro-6-(3,4-dimethoxyphenyl)-1,3-dimethyl-4-thioxo-2(1H)-pyrimidinone (1.51 g) in tetrahydrofuran (150 ml) was added methyl iodide (30 ml) and the mixture was refluxed for 90 minutes. The precipitate was added to 2,4,6-trimethylaniline (6 g) and the mixture was heated at 110°–120° C. for 3 hours. The reaction mixture was washed with a mixture of hexane and diisopropyl ether to remove excess 2,4,6-trimethylaniline. The resulting precipitate was collected by filtration and then dissolved in chloroform. The solution was washed with an aqueous solution of sodium bicarbonate, dried over magnesium sulfate and evaporated under reduced pressure to give crude product, which was purified by silica gel column chromatography to give 3,4-dihydro-6-(3,4-dimethoxyphenyl)-1,3-dimethyl-4-(2,4,6-trimethylphenylimino)-2(1H)-pyrimidinone (1.44 g); mp 68°–70° C. Thus obtained compound was recrystallized from a mixture of methanol and water (5:1) to give the desired compound as crystals.

mp 96°–98° C.

IR (Nujol): 1685, 1640, 1590 cm$^{-1}$

NMR (CDCl$_3$, δ): 6.8 (4H, s), 6.7 (1H, s), 5.13 (1H, s), 3.87 (3H, s), 3.85 (3H, s), 3.57 (3H, s), 3.14 (3H, s), 2.20 (3H, s), 2.00 (6H, s).

EXAMPLE 49

4-(4-Chloro-2-methylphenylimino)-3,4-dihydro-6-(3,4-dimethoxyphenyl)-1,3-dimethyl-2(1H)-pyrimidinone (0.17 g) was obtained according to the substantially same manner as that of Example 48 from 3,4-dihydro-6-(3,4-dimethoxyphenyl)-1,3-dimethyl-4-thioxo-2(1H)-pyrimidinone (0.2 g), methyl iodide (4 ml) and 4-chloro-2-methylaniline (0.4 g).

mp: 61°–66° C.

IR (Nujol): 1685, 1640, 1590 cm$^{-1}$

NMR (DMSO-d$_6$, δ): 7.3–6.6 (6H, m), 5.13 (1H, s), 3.75 (6H, s), 3.22 (3H, s), 3.09 (3H, s), 2.05 (3H, s).

EXAMPLE 50

3,4-Dihydro-6-(3,4-dimethoxyphenyl)-1,3-dimethyl-4-(3-pyridylimino)-2(1H)-pyrimidinone (1.1 g) was obtained according to the substantially same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and 3-aminopyridine (4.0 g).

The obtained compound was dissolved in ethyl acetate. To the solution was added a mixture of hydrochloric acid and ethyl acetate. The precipitate was collected by filtration, washed with diisopropyl ether and dried in vacuo to give 3,4-dihydro-6-(3,4-dimethoxyphenyl)-1,3-dimethyl-4-(3-pyridylimino)-2(1H)-pyrimidinone dihydrochloride (1.30 g).

mp: 145°–148° C.

IR (Nujol): 1710, 1610, 1580 cm$^{-1}$

NMR (D$_2$O, δ): 9.2–8.6 (3H, m), 8.30 (1H, dd, J=5.5, 8 Hz), 7.15 (3H, s), 6.23 (1H, s), 3.93 (3H, s), 3.90 (6H, s), 3.53 (3H, s).

EXAMPLE 51

4-(t-Butylamino)-3,4-dihydro-6-(3,4-dimethoxyphenyl)-1,3-dimethyl-2(1H)-pyrimidinone (0.57 g) was obtained according to the substantially same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and t-butylamine (10 ml).

mp: 153°–155° C.

IR (Nujol): 1680, 1650, 1605, 1595 cm$^{-1}$

NMR (DMSO-d$_6$, δ): 7.04 (3H, s), 5.66 (1H, s), 3.85 (6H, s), 3.20 (3H, s), 3.04 (3H, s), 1.25 (9H, s).

EXAMPLE 52

4-Cyclohexylimino-3,4-dihydro-1,3-dimethyl-6-(3,4-dimethoxyphenyl)-2(1H)-pyrimidinone (0.98 g) was obtained according to the substantially same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and cyclohexylamine (4.0 g).

mp: 116°–118° C.

IR (Nujol): 1680, 1650, 1600 cm$^{-1}$

NMR (DMSO-d$_6$, δ): 7.02 (3H, s), 5.83 (1H, s), 3.80 (6H, s), 3.2 (3H, s), 3.1–3.2 (1H, br), 3.03 (3H, s), 1.0–2.0 (10H, m).

EXAMPLE 53

3,4-Dihydro-4-(3,4-dimethoxybenzylimino)-6-(3,4-dimethoxyphenyl)-1,3-dimethyl-2(1H)-pyrimidinone (1.08 g) was obtained according to the substantially same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and 3,4-dimethoxybenzylamine (3.0 g).

mp: 141°–144° C.

IR (Nujol): 1660, 1640, 1590 cm$^{-1}$

NMR (CDCl$_3$, δ): 6.7–7.1 (6H, m), 5.7 (1H, s), 4.25 (2H, s), 3.9 (3H, s), 3.87 (3H, s), 3.85 (2H, s), 3.83 (3H, s), 3.47 (3H, s), 3.15 (3H, s).

EXAMPLE 54

3,4-Dihydro-1,3-dimethyl-6-phenyl-4-(2,4,6-trimethylphenylimino)-2(1H)-pyrimidinone (0.81 g) was obtained according to the substantially same manner as that of Example 48 from 3,4-dihydro-1,3-dimethyl-6-phenyl-4-thioxo-2(1H)-pyrimidinone (1.0 g), methyl iodide (22.7 ml) and 2,4,6-trimethylaniline (3.6 g).

mp: 136°–139° C.

IR (Nujol): 1680, 1650 cm$^{-1}$

NMR (DMSO-d$_6$, δ): 7.40 (5H, m), 6.10 (2H, s), 4.76 (1H, s), 3.46 (3H, s), 3.04 (3H, s), 2.13 (3H, s), 1.93 (6H, s).

EXAMPLE 55

3,4-Dihydro-6-(3,4-dimethoxyphenyl)-1,3-dimethyl-4-phenylimino-2(1H)-pyrimidinone (0.64 g) was obtained according to substantially the same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and aniline (3.0 g).

mp: 60°–64° C.

IR (Nujol): 1670, 1655, 1590 cm$^{-1}$

NMR (CDCl$_3$, δ): 6.6–7.5 (8H, m), 5.50 (1H, s), 3.86 (3H, s), 3.83 (3H, s), 3.53 (3H, s), 3.16 (3H, s).

EXAMPLE 56

3,4-Dihydro-6-(3,4-dimethoxyphenyl)-1,3-dimethyl-4-(3,4,5-trimethoxyphenylimino)-2(1H)-pyrimidinone (0.63 g) was obtained according to substantially the same manner as that of Example 48 from 3,4-dihydro-6-(3,4-dimethoxyphenyl)-1,3-dimethyl-2(1H)-pyrimidinone (1.0 g), methyl iodide (20 ml) and 3,4,5-trimethoxyaniline (3.0 g).

mp: 185°–188° C.

IR (Nujol): 1680, 1675, 1650 cm$^{-1}$

NMR (CDCl$_3$, δ): 6.7–6.95 (3H, m), 6.10 (2H, s), 5.60 (1H, s), 3.90 (3H, s), 3.87 (3H, s), 3.80 (9H, s), 3.52 (3H, s), 3.18 (3H, s).

EXAMPLE 57

3,4-Dihydro-6-(3,4-dimethoxyphenyl)-1,3-dimethyl-4-(2,4,6-trimethoxyphenylimino)-2(1H)-pyrimidinone (1.19 g) was obtained according to substantially the same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and 2,4,6-trimethoxyaniline (3.20 g).

mp: 173°–177° C.

IR (Nujol): 1680, 1640, 1590 cm$^{-1}$

NMR (CDCl$_3$, δ): 6.6–7.0 (3H, m), 6.18 (2H, s), 5.26 (1H, s), 3.89 (3H, s), 3.85 (3H, s), 3.77 (9H, s), 3.62 (3H, s), 3.15 (3H, s).

EXAMPLE 58

3,4-Dihydro-6-(3,4-dimethoxyphenyl)-1,3-dimethyl-4-(2,6-dimethylphenylimino)-2(1H)-pyrimidinone (0.75 g) was obtained according to substantially the same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and 2,6-dimethylaniline (2.0 g).

mp: 100°–104° C.

IR (Nujol): 1690, 1675, 1640 cm$^{-1}$

NMR (CDCl$_3$, δ): 6.6–7.2 (6H, m), 5.15 (1H, s), 3.91 (3H, s), 3.88 (3H, s), 3.65 (3H, s), 3.20 (3H, s), 2.10 (6H, s).

EXAMPLE 59

3,4-Dihydro-6-(3,4-dimethoxyphenyl)-1,3-dimethyl-4-(4-hydroxyphenylimino)-2(1H)-pyrimidinone (3.05 g) was obtained according to substantially the same manner as that of Example 48 from 3,4-dihydro-6-(3,4-dimethoxyphenyl)-1,3-dimethyl-4-thioxo-2(1H)-pyrimidinone (3.0 g), methyl iodide (60 ml) and 4-hydroxyaniline (4.5 g).

mp: 104°–108° C.

IR (Nujol): 1660, 1640 cm$^{-1}$

NMR (CDCl$_3$, δ): 6.82 (3H, s), 6.70 (4H, s), 3.87 (3H, s), 3.84 (3H, s), 3.50 (3H, s), 3.16 (3H, s).

EXAMPLE 60

3,4-Dihydro-6-(3,4-dimethoxyphenyl)-1,3-dimethyl-4-(5-methyl-1,3,4-thiadiazol-2-ylimino)-2(1H)-pyrimidinone (0.06 g) was obtained according to substantially the same manner as that of Example 48 from 3,4-dihydro-6-(3,4-dimethoxyphenyl)-1,3-dimethyl-4-thioxo-2(1H)-pyrimidinone (1.0 g), methyl iodide (20 ml) and 2-amino-5-methyl-1,3,4-thiadiazole (3.0 g).

mp: 206°–209° C.

IR (Nujol): 1680, 1620 cm$^{-1}$

NMR (DMSO-d$_6$, δ): 7.05 (3H, br.s), 6.50 (1H, s), 3.80 (3H, s), 3.77 (3H, s), 3.43 (3H, s), 3.25 (3H, s), 2.50 (3H, s).

EXAMPLE 61

3,4-Dihydro-1,3-dimethyl-6-(2,3,4-trimethoxyphenyl)-4-(2,4,6-trimethylphenylimino)-2(1H)-pyrimidinone (0.75 g) was obtained according to substantially the same manner as that of Example 48 from 3,4-dihydro-1,3-dimethyl-4-thioxo-6-(2,3,4-trimethoxyphenyl)-2(1H)-pyrimidinone (1.0 g), methyl iodide (35 ml) and 2,4,6-trimethylaniline (2.5 g).

mp: 48°–53° C.

IR (Nujol): 1690, 1640, 1600 cm$^{-1}$

NMR (CDCl$_3$, δ): 6.81 (2H, s), 6.73 (1H, d, J=9 Hz), 6.60 (1H, d, J=9 Hz), 5.12 (1H, s), 3.85 (6H, s), 3.80 (3H, s), 3.60 (3H, s), 3.08 (3H, s), 2.22 (3H, s), 2.04 (6H, s).

EXAMPLE 62

3,4-Dihydro-1,3-dimethyl-6-(4-methoxyphenyl)-4-(2,4,6-trimethylphenylimino)-2(1H)-pyrimidinone (2.6 g) was obtained according to substantially the same manner as that of Example 48 from 3,4-dihydro-1,3-dimethyl-6-(4-methoxyphenyl)-4-thioxo-2(1H)-pyrimidinone (2.1 g), methyl iodide (40 ml) and 2,4,6-trimethylaniline (9 ml).

mp: 50°–54° C.

IR (Nujol): 1690, 1650, 1610, 1590 cm$^{-1}$

NMR (DMSO-d$_6$, δ): 2.00 (6H, s), 2.16 (3H, s), 3.08 (3H, s), 3.60 (3H, s), 3.78 (3H, s), 4.88 (1H, s), 6.84 (2H, s), 7.00 (2H, d, J=9 Hz), 7.27 (2H, d, J=9 Hz).

EXAMPLE 63

3,4-Dihydro-1,3-dimethyl-6-(4-methoxy-2-methylphenyl)-4-(2,4,6-trimethylphenylimino)-2(1H)-pyrimidinone (1.67 g) was obtained according to substantially the same manner as that of Example 48 from 3,4-dihydro-1,3-dimethyl-6-(4-methoxy-2-methylphenyl)-4-thioxo-2(1H)-pyrimidinone (1.5 g), methyl iodide (25 ml) and 2,4,6-trimethylaniline (4.0 g).

mp: 57°–60° C.

IR (Nujol): 1690, 1650, 1610, 1590 cm$^{-1}$

NMR (CDCl$_3$, δ): 7.1–6.6 (5H, m), 5.08 (1H, s), 3.80 (3H, s), 3.61 (3H, s), 3.01 (3H, s), 2.22 (3H, s), 2.19 (3H, s), 2.03 (3H, s), 2.01 (3H, s).

EXAMPLE 64

3,4-Dihydro-6-(3,4-dimethoxyphenyl)-3-methyl-4-(2,4,6-trimethylphenylimino)-2(1H)-pyrimidinone (1.71 g) was obtained according to substantially the same manner as that of Example 48 from 3,4-dihydro-6-(3,4-dimethoxyphenyl)-3-methyl-4-thioxo-2(1H)-pyrimidinone (1.80 g), methyl iodide (36 ml) and 2,4,6-trimethylaniline (5.0 g).

mp: >300° C.

IR (Nujol): 1685, 1645, 1600 cm$^{-1}$

NMR (CDCl$_3$+CD$_3$OD, δ): 6.7–7.2 (5H, m), 5.36 (1H, s), 3.86 (6H, s), 3.50 (3H, s), 2.26 (3H, s), 2.03 (6H, s).

EXAMPLE 65

3,4-Dihydro-6-(3,4-dimethoxyphenyl)-3-methyl-1-n-propyl-4-(2,4,6-trimethylphenylimino)-2(1H)-pyrimidinone (0.5 g) was obtained according to substantially the same manner as that of Example 48 from 3,4-dihydro-6-(3,4-dimethoxyphenyl)-3-methyl-1-n-propyl-4-thioxo-2(1H)-pyrimidinone (1.0 g), methyl iodide (20 ml) and 2,4,6-trimethylaniline (3.0 g).

mp: 44°–48° C.

IR (Nujol): 1685, 1640, 1590 cm$^{-1}$

NMR (CDCl$_3$, δ): 6.65–6.9 (5H, m), 5.07 (1H, s), 3.67 (3H, s), 3.83 (3H, s), 3.57 (3H, s), 3.57 (2H, t, J=8 Hz), 2.20 (3H, s), 2.01 (6H, s), 1.3–1.9 (2H, m), 0.71 (3H, t, J=8 Hz).

EXAMPLE 66

1-Allyl-3,4-dihydro-6-(3,4-dimethoxyphenyl)-3-methyl-4-(2,4,6-trimethylphenylimino)-2(1H)-pyrimidinone (1.48 g) was obtained according to substantially the same manner as that of Example 48 from 1-allyl-3,4-dihydro-6-(3,4-dimethoxyphenyl)-3-methyl-4-thioxo- 2(1H)-pyrimidinone (1.8 g), methyl iodide (30.6 ml) and 2,4,6-trimethylaniline (6.4 ml).

mp: 63°–67° C.

IR (Nujol): 1685, 1640, 1590 cm$^{-1}$

NMR (DMSO-d$_6$, δ): 2.01 (6H, s), 2.19 (3H, s), 3.53 (3H, s), 3.78 (3H, s), 3.80 (3H, s), 4.23 (2H, m), 4.81–5.02 (2H, m), 4.91 (1H, s), 5.60–6.08 (1H, m), 6.75–7.04 (5H, m).

EXAMPLE 67

1-Benzyl-3,4-dihydro-6-(3,4-dimethoxyphenyl)-3-methyl-4-(2,4,6-trimethylphenylimino)-2(1H)-pyrimidinone (0.9 g) was obtained according to substantially the same manner as that of Example 48 from 1-benzyl-3,4-dihydro-6-(3,4-dimethoxyphenyl)-3-methyl-4-thioxo-2(1H)-pyrimidinone (2.8 g), methyl iodide (41.2 ml) and 2,4,6-trimethylaniline (8.5 ml).

mp: 144°–146° C.

IR (Nujol): 1695, 1640, 1600, 1590 cm$^{-1}$

NMR (DMSO-d$_6$, δ): 2.02 (6H, s), 2.16 (3H, s), 3.44 (3H, s), 3.52 (3H, s), 3.73 (3H, s), 4.85 (2H, s), 4.95 (1H, s), 6.61–7.40 (10H, m).

EXAMPLE 68

3,4-Dihydro-1,3-dimethyl-4-(2,4,6-trimethylphenylimino)-2(1H)-pyrimidinone (0.74 g) was obtained according to substantially the same manner as that of Example 48 from 3,4-dihydro-1,3-dimethyl-4-thioxo-2(1H)-pyrimidinone (0.74 g), methyl iodide (18 ml) and 2,4,6-trimethylaniline (3.9 g).

mp: 91°–93° C.

IR (Nujol): 1680, 1655 cm$^{-1}$

NMR (DMSO-d$_6$, δ): 1.92 (6H, s), 2.20 (3H, s), 3.23 (3H, s), 3.40 (3H, s), 5.00 (1H, d, J=8 Hz), 6.82 (2H, s), 7.10 (1H, d, J=8 Hz).

EXAMPLE 69

3,4-Dihydro-6-(3,4-dimethoxyphenyl)-1-methyl-4-(2,4,6-trimethylphenylimino)-2(1H)-pyrimidinone (0.82 g) was obtained according to substantially the same manner as that of Example 48 from 3,4-dihydro-6-(3,4-dimethoxyphenyl)-1-methyl-4-thioxo-2(1H)-pyrimidinone (1.0 g), methyl iodide (3.5 ml) and 2,4,6-trimethylaniline (1.51 ml).

mp 233°–236° C.

IR (Nujol): 1635 cm$^{-1}$

NMR (CDCl$_3$+CD$_3$OD, δ): 6.55–6.9 (5H, m), 5.08 (1H, s), 3.83 (3H, s), 3.80 (3H, s), 3.23 (3H, s), 2.23 (3H, s), 2.17 (6H, s).

EXAMPLE 70

3,4-Dihydro-6-(3,4-dimethoxyphenyl)-3-methyl-4-(2,4,6-trimethylphenylimino)-2(1H)-pyrimidinone (0.54 g) was obtained according to substantially the same manner as that of Example 48 from 3,4-dihydro-6-(3,4-dimethoxyphenyl)-2-isopropoxy-3-methyl-4-thioxopyrimidine (0.8 g) methyl iodide (10 ml) and 2,4,6-trimethylaniline (2.0 g).

mp: >300° C.

IR (Nujol): 1685, 1645, 1600 cm$^{-1}$

EXAMPLE 71

To a solution of 3,4-dihydro-6-(3,4-dichlorophenyl)-1,3-dimethyl-4-thioxo-2(1H)-pyrimidinone (1.0 g) in toluene (100 ml) was added methyl iodide (20 ml) and the mixture was refluxed for 3 hours. Another methyl iodide (20 ml) was added thereto, and the mixture was refluxed for further 5 hours. After being cooled, the mixture was evaporated under reduced pressure. To the resulting oil was added 2,4,6-trimethylaniline (3.0 g), and the mixture was stirred at 120° C. for 4 hours. The resulting oil was dissolved in ethyl acetate and washed successively with an aqueous solution of sodium bicarbonate and water. After being dried over magnesium sulfate, the solution was evaporated under reduced pressure. The residue was subjected to column chromatography on silica gel eluting with chloroform to give 3,4-dihydro-6-(3,4-dichlorophenyl)-1,3-dimethyl-4-(2,4,6-trimethylphenylimino)-2(1H)-pyrimidinone (0.56 g).

mp: 194°–198° C.

IR (Nujol): 1700, 1645, 1600 cm$^{-1}$

NMR (CDCl$_3$, δ): 7.42 (1H, d, J=8 Hz), 7.28 (1H, d, J=2 Hz), 7.02 (1H, dd, J=8 Hz, 2 Hz), 6.80 (2H, br.s), 5.10 (1H, s), 3.57 (3H, s), 3.10 (3H, s), 2.20 (3H, s), 2.02 (6H, s).

EXAMPLE 72

To a solution of 3,4-dihydro-6-(3,4-dimethoxyphenyl)-1-ethyl-3-methyl-4-thioxo-2(1H)-pyrimidinone (0.59 g) in tetrahydrofuran (50 ml) was added methyl iodide (10 ml) and the mixture was refluxed for 90 minutes. The precipitate was added to 2,4,6-trimethylaniline (2 g) and the mixture was heated at 110°–120° C. for 3 hours. The reaction mixture was washed with a mixture of hexane and diisopropyl ether to remove excess 2,4,6-trimethylaniline. The resulting precipitate was collected by filtration and then dissolved in chloroform. The solution was washed with an aqueous solution of sodium bicarbonate, dried over magnesium sulfate and evaporated under reduced pressure to give crude product, which was purified by silica gel column chromatography to give 3,4-dihydro-6-(3,4-dimethoxyphenyl)-1-ethyl-3-methyl-4-(2,4,6-trimethylphenylimino)-2(1H)-pyrimidinone (0.29 g); mp 57°–61° C. Thus obtained compound was recrystallized from a mixture of ethanol and water (3:1) to give the desired compound as crystals.

mp 116°–118° C.

IR (Nujol): 1685, 1660, 1600 cm$^{-1}$

NMR (CDCl$_3$, δ): 6.6–6.9 (5H, m), 5.07 (1H, s), 3.85 (3H, s), 3.83 (3H, s), 3.80 (2H, q, J=7 Hz), 3.57 (3H, s), 2.20 (3H, s), 2.02 (6H, s), 1.12 (3H, t, J=7 Hz).

EXAMPLE 73

1,3-Diethyl-3,4-dihydro-6-(3,4-dimethoxyphenyl)-4-(2,4,6-trimethylphenylimino)-2(1H)-pyrimidinone (0.69 g) was obtained according to the substantially same manner as that of Example 72 from 1,3-diethyl-3,4-dihydro-6-(3,4-dimethoxyphenyl)-4-thioxo-2(1H)-pyrimidinone (1.0 g) methyl iodide (40 ml) and 2,4,6-trimethylaniline (3.0 g), except that toluene was used as solvent in the place of tetrahydrofuran.

mp: 122°–124° C.

IR (Nujol): 1680, 1650, 1605 cm$^{-1}$

NMR (CDCl$_3$, δ): 6.85–6.9 (5H, m), 5.06 (1H, s), 4.32 (2H, q, J=7 Hz), 3.87 (6H, s), 3.68 (2H, q, J=7 Hz), 2.21 (3H, s), 2.03 (6H, s), 1.38 (3H, t, J=7 Hz), 1.12 (3H, t, J=7 Hz).

EXAMPLE 74

3,4-Dihydro-1,3-dimethyl-6-(3,4,5-trimethoxyphenyl)-4-(2,4,6-trimethylphenylimino)-2(1H)-pyrimidinone (0.39 g) was obtained according to the substantially same manner as that of Example 72 from 3,4-dihydro-1,3-dimethyl-4-thioxo-6-(3,4,5-trimethoxyphenyl)-2(1H)-pyrimidinone (0.59 g), methyl iodide (2.2 ml) and 2,4,6-trimethylaniline (2.1 g).

mp: 128°–131° C.

IR(Nujol): 1675, 1640 cm$^{-1}$

NMR (DMSO-d$_6$, δ): 1.97 (6H, s), 2.16 (3H, s), 3.07 (3H, s), 3.46 (3H, s), 3.66 (3H, s), 3.73 (6H, s), 4.88 (1H, s), 6.67 (2H, s), 6.80 (2H, s).

EXAMPLE 75

To a solution of 3,4-dihydro-1,3-dimethyl-6-(3-pyridyl)-4-thioxo-2(1H)-pyrimidinone (1.2 g) in tetrahydrofuran (12 ml) was added a mixture of hydrochloric acid and ethyl acetate. The precipitate was collected by filtration, washed with ethyl acetate and dissolved in N,N-dimethylformamide (25 ml). To the solution was added methyl iodide (10 ml) and stirred at 60° C. for 40 minutes. The resulting solution was evaporated under reduced pressure. The residue was added to 2,4,6-trimethylaniline (10 ml). After heating at 120° C. for 2 hours, the mixture was cooled to ambient temperature. The precipitate was collected by filtration to give 3,4-dihydro-1,3-dimethyl-6-(1-methyl-3-pyridinio)-4-(2,4,6-trimethylphenylimino)-2(1H)-pyrimidinone iodide (1.75 g).

IR(Nujol): 1680, 1645, 1630, 1080, 860 cm$^{-1}$

NMR(DMSO-d$_6$, δ): 1.93–2.30 (9H, m), 3.05 (3H, s), 3.45 (3H, s), 4.33 (3H, s), 6.66 (1H, s), 6.78 (2H, s), 8.20 (1H, m), 8.67 (1H, m), 9.10 (2H, m).

EXAMPLE 76

To a mixture of 3,4-dihydro-6-(3,4-dimethoxyphenyl)-3-methyl-4-thioxo-2(1H)-pyrimidinone (2.7 g) in tetrahydrofuran (24 ml) was added methyl iodide (12 ml) and the mixture was refluxed for 3 hours. The precipitate was collected by filtration and added to 2,4,6-trimethylaniline (4.1 ml). The mixture was stirred at 90° C. for 5 hours and hexane (10 ml) was added thereto. The precipitate was collected by filtration and washed successively with hexane, aqueous sodium hydroxide, ethanol and diisopropyl ether to give 3,4-dihydro-6-(3,4-dimethoxyphenyl)-3-methyl-4-(2,4,6-trimethylphenylimino)-2(1H)-pyrimidinone (2.75 g).

IR (Nujol): 1685, 1645, 1600 cm$^{-1}$

EXAMPLE 77

3,4-Dihydro-6-(3,4-dimethoxyphenyl)-4-(2,4,6-trimethylphenylimino)-2(1H)-pyrimidinone (0.62 g) was obtained according to substnatially the same manner as that of Example 48 from 3,4-dihydro-6-(3,4-dimethoxyphenyl)-4-thioxo-2(1H)-pyrimidinone (0.6 g), methyl iodide (3 ml) and 2,4,6-trimethylaniline (3 ml).

mp 258°–261° C.

IR (Nujol): 1640 cm$^{-1}$

NMR (CDCl$_3$, δ): 6.5–7.4 (5H, m), 5.32 (1H, s), 3.83 (3H, s), 3.77 (3H, s), 2.26 (3H, s), 2.14 (6H, s).

EXAMPLE 78

To a solution of 3,4-dihydro-6-(3,4-dimethoxyphenyl)-1,3-dimethyl-4-(4-hydroxyphenylimino)-2(1H)-pyrimidinone (1.5 g) in acetone (30 ml) was added potassium carbonate (0.56 g) and epichlorohydrin (0.32 ml). After the mixture was refluxed for 7 hours, an additional epichlorohydrin (1.6 ml) was added thereto, and further the mixture was refluxed for 38 hours. The resulting mixture was evaporated and chromatographed on silica-gel eluting with chloroform to give crude 3,4-dihydro-6-(3,4-dimethoxyphenyl)-1,3-dimethyl-4-[4-(2,3-epoxypropoxy)phenylimino]-2(1H)-pyrimidinone, which was recrystallized from diethyl ether.

mp: 155°–157° C.

IR (Nujol): 1680, 1640, 1590 cm$^{-1}$

NMR (CDCl$_3$, δ): 6.6–7.0 (7H, m), 5.51 (1H, s), 3.9–4.3 (2H, m), 3.87 (3H, s), 3.84 (3H, s), 3.50 (3H, s), 3.2–3.4 (1H, s), 3.16 (3H, s), 2.6–3.0 (2H, m).

EXAMPLE 79

To a solution of 3,4-dihydro-6-(3,4-dimethoxyphenyl)-1,3-dimethyl-4-[4-(2,3-epoxypropoxy)-phenylimino]-2(1H)-pyrimidinone (1.0 g) in ethanol (30 ml) was added isopropylamine (2.0 ml). The mixture was refluxed for 2 hours. After being cooled, the resulting mixture was evaporated and triturated with diisopropyl ether to give 3,4-dihydro-6-(3,4-dimethoxyphenyl)-1,3-dimethyl-4-[4-(3-isopropylamino-2-hydroxypropoxy)phenylimino]-2(1H)-pyrimidinone (1.13 g).

mp: 129°–132° C.

IR (Nujol): 1685, 1645, 1605 cm$^{-1}$

NMR (CDCl$_3$, δ): 6.6–7.1 (7H, m), 5.53 (1H, s), 3.9–4.1 (3H, m), 3.90 (3H, s), 3.87 (3H, s), 3.53 (3H, s), 3.17 (3H, s), 2.6–3.0 (3H, m), 2.4 (2H, br.s), 1.08 (6H, d, J=6 Hz).

EXAMPLE 80

To a suspension of 3,4-dihydro-6-(3,4-dimethoxyphenyl)-1-ethyl-3-methyl-4-(2,4,6-trimethylphenylimino)-2(1H)-pyrimidinone (11.3 g) in water (20 ml) was added conc. hydrochloric acid (3.1 ml) and the mixture was evaporated under reduced pressure. To the residue was added ethanol (20 ml) and evaporated under reduced pressure again. The residue was crystallized from a mixture of diisopropyl ether and methanol (1:1) to give 3,4-dihydro-6-(3,4-dimethoxyphenyl)-1-ethyl-3-methyl-4-(2,4,6-trimethylphenylimino)-2(1H)-pyrimidinone hydrochloride (9.9 g).

mp 132°–134° C.

IR (Nujol): 1720, 1700, 1620 cm$^{-1}$

NMR (DMSO-d$_6$, δ): 6.6–7.3(5H, m), 5.13(1H, s), 3.86 (3H, s), 3.83(3H, s), 3.78(3H, s) 3.60(2H, q, J=7 Hz), 2.24(9H, s), 1.20(3H, t, J=7 Hz).

EXAMPLE 81

3,4-Didydro-6-(3,4-dimethoxyphenyl)-1,3-dimethyl-4-(2,4,6-trimethylphenylimino)-2(1H)-pyrimidinone hydrochloride was obtained according to substantially the same manner as that of Example 80.

mp 100°–110° C.

IR (Nujol): 1710, 1630 cm$^{-1}$

NMR (DMSO-d$_6$, δ): 6.8–7.3 (5H, m), 5.15 (1H, s), 3.84 (3H, s), 3.78 (3H, s), 3.76 (3H, s), 3.31 (3H, s), 2.27 (3H, s), 2.20 (6H, s).

What we claim is:

1. A compound of the formula:

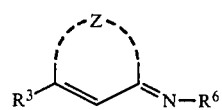

wherein Z is a group selected from

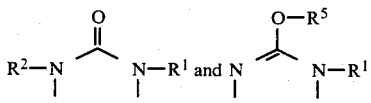

in which $R^1$ and $R^2$ are each hydrogen or $C_1$–$C_6$ alkyl and $R^5$ is $C_1$–$C_6$ alkyl, $R^3$ is phenyl or phenyl substituted with mono-, di- or tri-$C_1$–$C_6$ alkyl, or with mono-, di- or tri-$C_1$–$C_6$ alkoxy, or with mono- or di-halogen, $R^6$ is phenyl substituted with mono-, di- or tri-$C_1$–$C_6$ alkyl, or with mono-, di- or tri-$C_1$–$C_6$ alkoxy, or with mono- or di-hydroxy, or with mono- or di-halogen, or with halogen and $C_1$–$C_6$ alkyl, and pharmaceutically acceptable salts thereof.

2. A compound of claim 1, wherein Z is a group of the formula:

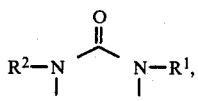

in which $R^1$ and $R^2$ are each as defined above.

3. A compound of claim 2, wherein $R^3$ is phenyl substituted with mono-, di- or tri $C_1$–$C_6$ alkoxy.

4. A compound of claim 3, wherein $R^6$ is phenyl substituted with mono-, or tri $C_1$–$C_6$ alkyl, or with mono-, or tri $C_1$–$C_6$ alkoxy or with hydroxy.

5. A compound of claim 4, wherein $R^3$ is 3,4-dimethoxyphenyl.

6. A compound of claim 5, wherein $R^6$ is 2,4,6-trimethoxyphenyl.

7. A compound of claim 5, wherein $R^6$ is 2,4,6-trimethylphenyl.

8. A compound of claim 7, which is 3,4-dihydro-6-(3,4-dimethoxyphenyl)-1,3-dimethyl-4-(2,4,6-trimethylphenylimino)-2(1H)-pyrimidinone.

9. A compound of claim 7, which is 3,4-dihydro-6-(3,4-dimethoxyphenyl)-1-ethyl-3-methyl-4-(2,4,6-trimethylphenylimino)-2(1H)-pyrimidinone.

10. A compound of claim 7, which is 3,4-dihydro-6-(3,4-dimethoxyphenyl)-3-methyl-4-(2,4,6-trimethylphenylimino)-2(1H)-pyrimidinone.

11. A compound of claim 6, which is 3,4-dihydro-6-(3,4-dimethoxyphenyl)-1,3-dimethyl-4-(2,4,6-trimethoxyphenylimino)-2(1H)-pyrimidinone.

12. A compound of claim 1, wherein Z is a group of the formula:

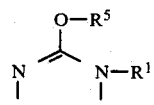

in which $R^1$ and $R^5$ are each as defined above.

13. A compound of claim 12, which is 3,4-dihydro-6-(3,4-dimethoxyphenyl)-2-ethoxy-3-methyl-4-(2,4,6-trimethylphenylimino)pyrimidine.

14. A cardiotonic pharmaceutical composition comprising an effective cardiotonic amount of a compound of claim 1 in association with a pharmaceutically acceptable, substantially nontoxic carrier or excipient.

15. An antihypertensive pharmaceutical composition comprising an effective anti-hypertensive amount of a compound of claim 1 in terms of antihypertension in association with a pharmaceutically acceptable, substantially nontoxic carrier or excipient.

16. A cerebrovascular vasodilative pharmaceutical composition comprising an effective cerebrovascular vasodilative amount of a compound of claim 1 in terms of cerebrovascular vasodilation in association with a pharmaceutically acceptable, substantially nontoxic carrier or excipient.

17. An anti-platelet aggregation pharmaceutical composition comprising an effective anti-platelet aggregation amount of a compound of claim 1 in terms of anti-platelet aggregation in association with a pharmaceutically acceptable, substantially nontoxic carrier or excipient.

* * * * *